(12) United States Patent
McGuckin, Jr. et al.

(10) Patent No.: US 9,463,005 B2
(45) Date of Patent: Oct. 11, 2016

(54) VASCULAR HOLE CLOSURE DEVICE

(71) Applicants: James F. McGuckin, Jr., Radnor, PA (US); John D. Leedle, Philadelphia, PA (US); James S. Tarmin, Philadelphia, PA (US); Thanu Anidharan, Downingtown, PA (US); Stephan A. DeFonzo, Wayne, PA (US)

(72) Inventors: James F. McGuckin, Jr., Radnor, PA (US); John D. Leedle, Philadelphia, PA (US); James S. Tarmin, Philadelphia, PA (US); Thanu Anidharan, Downingtown, PA (US); Stephan A. DeFonzo, Wayne, PA (US)

(73) Assignee: Rex Medical, L.P., Conshocken, PA (US)

( * ) Notice: Subject to any disclaimer, the term of this patent is extended or adjusted under 35 U.S.C. 154(b) by 573 days.

(21) Appl. No.: 13/673,995

(22) Filed: Nov. 10, 2012

(65) Prior Publication Data

US 2013/0066364 A1 Mar. 14, 2013

Related U.S. Application Data

(63) Continuation of application No. 12/854,988, filed on Aug. 12, 2010, now abandoned, which is a continuation-in-part of application No. 12/358,411, filed on Jan. 23, 2009, now Pat. No. 8,070,772.

(60) Provisional application No. 61/241,555, filed on Sep. 11, 2009, provisional application No. 61/066,072, filed on Feb. 15, 2008.

(51) Int. Cl.
*A61B 17/04* (2006.01)
*A61B 17/00* (2006.01)

(52) U.S. Cl.
CPC .. *A61B 17/0057* (2013.01); *A61B 2017/00004* (2013.01); *A61B 2017/00659* (2013.01); *A61B 2017/0456* (2013.01); *A61B 2017/0459* (2013.01)

(58) Field of Classification Search
CPC .......... A61B 17/0057; A61B 17/0401; A61B 2017/00575; A61B 2017/00592; A61B 2017/00601; A61B 2017/00606; A61B 2017/0061; A61B 2017/00615; A61B 2017/00619; A61B 2017/00628; A61B 2017/00632; A61B 2017/00637; A61B 2017/00641; A61B 2017/00646; A61B 2017/00654; A61B 2017/00659; A61B 2017/0414; A61B 2017/0417; A61B 2017/0419; A61B 2017/0403; A61B 2017/0404; A61B 2017/0406; A61B 2017/0408; A61B 2017/0446; A61B 2017/0448; A61B 2017/045; A61B 2017/0451; A61B 2017/0456; A61B 2017/0459; A61B 2017/0461; A61B 2017/0462
USPC ................ 606/151–154, 157, 213, 215, 216, 606/218–221
See application file for complete search history.

(56) References Cited

U.S. PATENT DOCUMENTS 2,024,871 A 12/1935 Parsons
2,398,220 A 4/1946 Gelpcke
(Continued)

FOREIGN PATENT DOCUMENTS

DE 19604817 8/1997
EP 0637431 2/1995
(Continued)

*Primary Examiner* — Dianne Dornbusch
(74) *Attorney, Agent, or Firm* — Neil D. Gershon

(57) ABSTRACT

A device for closing an aperture in a vessel wall comprising a covering member having a longitudinal axis and positionable inside the vessel against the internal opening of the aperture and having a dimension to prevent egress of fluid through the aperture and having a first opening. A first retainer is positionable external of the vessel. A flexible connecting member operatively connects the covering member and the first retainer, wherein the first opening of the covering member is configured to restrict movement of the connecting member.

14 Claims, 18 Drawing Sheets

(56) References Cited

U.S. PATENT DOCUMENTS

| | | | |
|---|---|---|---|
| 2,413,142 A | 12/1946 | Jones et al. | |
| 3,467,089 A | 9/1969 | Hasson | |
| 3,516,403 A | 6/1970 | Coumut | |
| 3,527,223 A | 9/1970 | Melvin | |
| 3,675,648 A | 7/1972 | Pharriss et al. | |
| 3,842,827 A | 10/1974 | Jacobs | |
| 3,874,388 A | 4/1975 | King et al. | |
| 3,913,573 A | 10/1975 | Gutnick | |
| 3,937,217 A | 2/1976 | Kosonen | |
| 3,958,576 A | 5/1976 | Komiya | |
| 3,976,079 A | 8/1976 | Samuels et al. | |
| 4,007,743 A | 2/1977 | Blake | |
| 4,031,569 A | 6/1977 | Jacob | |
| 4,117,838 A | 10/1978 | Hasson | |
| 4,286,497 A | 9/1981 | Shamah | |
| 4,317,445 A | 3/1982 | Robinson | |
| 4,485,816 A | 12/1984 | Krumme | |
| 4,505,274 A | 3/1985 | Speelman | |
| 4,512,338 A | 4/1985 | Balko et al. | |
| 4,532,926 A | 8/1985 | O'Holla | |
| 4,610,671 A | 9/1986 | Luther | |
| 4,615,514 A | 10/1986 | Hamlin | |
| 4,638,803 A | 1/1987 | Rand | |
| 4,665,906 A | 5/1987 | Jervis | |
| 4,676,245 A | 6/1987 | Fukuda | |
| 4,705,040 A * | 11/1987 | Mueller | A61B 17/00234 604/513 |
| 4,744,364 A | 5/1988 | Kensey | |
| 4,796,612 A | 1/1989 | Reese | |
| 4,836,204 A | 6/1989 | Landymore et al. | |
| 4,890,612 A | 1/1990 | Kensey | |
| 4,917,089 A | 4/1990 | Sideris | |
| 4,924,866 A | 5/1990 | Yoon | |
| 4,971,068 A | 11/1990 | Sahi | |
| 5,009,663 A | 4/1991 | Broome | |
| 5,021,059 A * | 6/1991 | Kensey | A61B 17/0057 604/15 |
| 5,047,047 A | 9/1991 | Yoon | |
| 5,061,274 A | 10/1991 | Kensey | |
| 5,108,420 A | 4/1992 | Marks | |
| 5,108,421 A | 4/1992 | Fowler | |
| 5,123,913 A | 6/1992 | Wilk et al. | |
| 5,123,914 A | 6/1992 | Cope | |
| 5,171,252 A | 12/1992 | Friedland | |
| 5,171,259 A | 12/1992 | Inoue | |
| 5,192,300 A | 3/1993 | Fowler | |
| 5,192,301 A | 3/1993 | Kamiya et al. | |
| 5,192,302 A | 3/1993 | Kensey et al. | |
| 5,219,359 A | 6/1993 | McQuilkin et al. | |
| 5,222,974 A | 6/1993 | Kensey et al. | |
| 5,246,441 A | 9/1993 | Ross et al. | |
| 5,269,809 A | 12/1993 | Hayhurst et al. | |
| 5,279,572 A | 1/1994 | Hokama | |
| 5,282,827 A | 2/1994 | Kensey et al. | |
| 5,292,332 A | 3/1994 | Lee | |
| 5,306,254 A | 4/1994 | Nash et al. | |
| 5,312,435 A | 5/1994 | Nash et al. | |
| 5,318,040 A | 6/1994 | Kensey et al. | |
| 5,334,210 A | 8/1994 | Gianturco | |
| 5,350,399 A | 9/1994 | Erlebacher et al. | |
| 5,350,400 A | 9/1994 | Esposito et al. | |
| 5,370,661 A | 12/1994 | Branch | |
| 5,372,146 A | 12/1994 | Branch | |
| 5,385,554 A | 1/1995 | Brimhall | |
| RE34,866 E | 2/1995 | Kensey et al. | |
| 5,391,183 A | 2/1995 | Janzen et al. | |
| 5,409,444 A | 4/1995 | Kensey et al. | |
| 5,411,520 A | 5/1995 | Nash et al. | |
| 5,433,727 A | 7/1995 | Sideris | |
| 5,441,517 A | 8/1995 | Kensey et al. | |
| 5,443,481 A | 8/1995 | Lee | |
| 5,451,235 A | 9/1995 | Lock et al. | |
| 5,474,557 A | 12/1995 | Mai | |
| 5,478,352 A | 12/1995 | Fowler | |
| 5,478,353 A | 12/1995 | Yoon | |
| 5,486,195 A | 1/1996 | Myers et al. | |
| 5,507,754 A | 4/1996 | Green et al. | |
| 5,520,691 A | 5/1996 | Branch | |
| 5,531,759 A | 7/1996 | Kensey et al. | |
| 5,540,716 A | 7/1996 | Hlavacek | |
| 5,545,178 A | 8/1996 | Kensey et al. | |
| 5,549,617 A | 8/1996 | Green et al. | |
| 5,549,633 A | 8/1996 | Evans et al. | |
| 5,591,204 A | 1/1997 | Janzen et al. | |
| 5,593,422 A | 1/1997 | Muijs Van de Moer et al. | |
| 5,620,461 A | 4/1997 | Muijs Van De Moer et al. | |
| 5,630,833 A | 5/1997 | Katsaros et al. | |
| 5,634,936 A | 6/1997 | Linden et al. | |
| 5,643,317 A | 7/1997 | Pavcnik et al. | |
| 5,649,959 A | 7/1997 | Hannam et al. | |
| 5,658,313 A | 8/1997 | Thal | |
| 5,662,681 A | 9/1997 | Nash et al. | |
| 5,674,231 A | 10/1997 | Green et al. | |
| 5,676,689 A | 10/1997 | Kensey et al. | |
| 5,690,674 A | 11/1997 | Diaz | |
| 5,700,277 A * | 12/1997 | Nash | A61B 17/0057 128/887 |
| 5,702,421 A | 12/1997 | Schneidt | |
| 5,707,393 A | 1/1998 | Kensey et al. | |
| 5,709,707 A | 1/1998 | Lock et al. | |
| 5,725,498 A | 3/1998 | Janzen et al. | |
| 5,728,132 A | 3/1998 | Van Tassel et al. | |
| 5,728,133 A | 3/1998 | Kontos | |
| 5,735,875 A | 4/1998 | Bonutti et al. | |
| 5,735,877 A * | 4/1998 | Pagedas | A61B 17/0487 606/148 |
| 5,741,223 A | 4/1998 | Janzen | |
| 5,741,297 A | 4/1998 | Simon | |
| 5,766,206 A | 6/1998 | Wijkamp et al. | |
| 5,769,894 A | 6/1998 | Ferragamo | |
| 5,782,860 A | 7/1998 | Epstein et al. | |
| 5,782,861 A | 7/1998 | Cragg et al. | |
| 5,810,845 A | 9/1998 | Yoon | |
| 5,810,846 A | 9/1998 | Virnich et al. | |
| 5,810,884 A | 9/1998 | Kim | |
| 5,814,056 A | 9/1998 | Prosst et al. | |
| 5,820,628 A | 10/1998 | Middleman et al. | |
| 5,861,003 A | 1/1999 | Latson et al. | |
| 5,893,856 A | 4/1999 | Jacob et al. | |
| 5,910,155 A | 6/1999 | Ratcliff et al. | |
| 5,916,235 A | 6/1999 | Guglielmi | |
| 5,916,236 A | 6/1999 | Muijs Van de Moer et al. | |
| 5,919,207 A | 7/1999 | Taheri | |
| 5,964,782 A | 10/1999 | Lafontaine et al. | |
| 5,976,159 A | 11/1999 | Bolduc et al. | |
| 5,976,174 A | 11/1999 | Ruiz | |
| 5,984,933 A | 11/1999 | Yoon | |
| 5,984,949 A | 11/1999 | Levin | |
| 5,989,268 A | 11/1999 | Pugsley, Jr. et al. | |
| 6,001,110 A | 12/1999 | Adams | |
| 6,007,563 A | 12/1999 | Nash et al. | |
| 6,010,517 A | 1/2000 | Baccaro | |
| 6,015,417 A | 1/2000 | Reynolds, Jr. | |
| 6,024,756 A | 2/2000 | Huebsch et al. | |
| 6,033,427 A | 3/2000 | Lee | |
| 6,045,551 A | 4/2000 | Bonutti | |
| 6,048,357 A | 4/2000 | Kontos | |
| 6,048,358 A | 4/2000 | Barak | |
| 6,056,768 A | 5/2000 | Cates et al. | |
| 6,063,085 A | 5/2000 | Tay et al. | |
| 6,063,106 A | 5/2000 | Gibson | |
| 6,066,160 A * | 5/2000 | Colvin | A61B 17/0487 606/151 |
| 6,071,300 A | 6/2000 | Brenneman et al. | |
| 6,077,281 A | 6/2000 | Das | |
| 6,077,291 A | 6/2000 | Das | |
| 6,080,182 A | 6/2000 | Shaw et al. | |
| 6,080,183 A | 6/2000 | Tsugita et al. | |
| 6,110,207 A | 8/2000 | Eichhorn et al. | |
| 6,113,611 A | 9/2000 | Allen et al. | |
| 6,117,159 A | 9/2000 | Huebsch et al. | |
| 6,117,161 A | 9/2000 | Li et al. | |
| 6,120,524 A | 9/2000 | Taheri | |
| 6,126,675 A | 10/2000 | Shchervinsky et al. | |

(56) References Cited

U.S. PATENT DOCUMENTS

| | | | |
|---|---|---|---|
| 6,136,010 A | 10/2000 | Modesitt et al. |
| 6,139,564 A | 10/2000 | Teoh |
| 6,152,948 A | 11/2000 | Addis |
| 6,162,240 A | 12/2000 | Cates et al. |
| 6,171,320 B1 | 1/2001 | Monassevitch |
| 6,171,329 B1 | 1/2001 | Shaw et al. |
| 6,174,322 B1 | 1/2001 | Schneidt |
| 6,179,863 B1 | 1/2001 | Kensey et al. |
| 6,197,042 B1 | 3/2001 | Ginn et al. |
| 6,206,893 B1 | 3/2001 | Klein et al. |
| 6,206,907 B1 | 3/2001 | Marino et al. |
| 6,228,096 B1 | 5/2001 | Marchand |
| 6,231,561 B1 | 5/2001 | Frazier et al. |
| 6,231,592 B1 | 5/2001 | Bonutti et al. |
| 6,251,122 B1 | 6/2001 | Tsukernik |
| 6,261,309 B1 | 7/2001 | Urbanski |
| 6,264,673 B1 | 7/2001 | Egnelöv |
| 6,270,515 B1 | 8/2001 | Linden et al. |
| 6,277,140 B2 | 8/2001 | Ginn et al. |
| 6,290,674 B1 | 9/2001 | Roue et al. |
| 6,293,961 B2 | 9/2001 | Schwartz et al. |
| 6,312,446 B1 | 11/2001 | Huebsch |
| 6,328,727 B1 | 12/2001 | Frazier et al. |
| 6,334,865 B1 | 1/2002 | Redmond et al. |
| 6,336,914 B1 | 1/2002 | Gillespie et al. |
| 6,342,064 B1 | 1/2002 | Koike et al. |
| 6,346,117 B1 | 2/2002 | Greenhalgh |
| 6,348,053 B1 | 2/2002 | Cachia |
| 6,350,270 B1 | 2/2002 | Roue |
| 6,350,274 B1 | 2/2002 | Li |
| 6,355,052 B1 | 3/2002 | Neuss et al. |
| 6,368,341 B1 | 4/2002 | Abrahamson |
| 6,368,343 B1 | 4/2002 | Bonutti et al. |
| 6,391,037 B1 | 5/2002 | Greenhalgh |
| 6,391,048 B1 | 5/2002 | Ginn et al. |
| 6,409,739 B1 | 6/2002 | Nobles et al. |
| 6,414,664 B1 | 7/2002 | Conover et al. |
| 6,419,669 B1 | 7/2002 | Frazier et al. |
| 6,425,911 B1 | 7/2002 | Akerfeldt et al. |
| 6,436,088 B2 | 8/2002 | Frazier et al. |
| 6,440,152 B1 | 8/2002 | Gainor et al. |
| 6,447,042 B1 | 9/2002 | Jin |
| 6,447,524 B1 | 9/2002 | Knodel et al. |
| 6,451,030 B2 | 9/2002 | Li et al. |
| 6,468,293 B2 | 10/2002 | Bonutti et al. |
| 6,482,179 B1 | 11/2002 | Chu et al. |
| 6,491,714 B1 | 12/2002 | Bennett |
| 6,500,184 B1 | 12/2002 | Chan et al. |
| 6,503,266 B1 | 1/2003 | Sjögren |
| 6,508,828 B1 | 1/2003 | Akerfeldt et al. |
| 6,537,299 B1 | 3/2003 | Hogendijk et al. |
| 6,547,806 B1 | 4/2003 | Ding |
| 6,569,185 B2 | 5/2003 | Ungs |
| 6,569,187 B1 | 5/2003 | Bonutti et al. |
| 6,585,748 B1 | 7/2003 | Jeffree |
| 6,585,750 B2 | 7/2003 | Bonutti et al. |
| 6,596,012 B2 | 7/2003 | Akerfeldt et al. |
| 6,626,937 B1 | 9/2003 | Cox |
| 6,635,073 B2 | 10/2003 | Bonutti |
| 6,648,903 B1 | 11/2003 | Pierson, III |
| 6,663,653 B2 | 12/2003 | Akerfeldt |
| 6,663,655 B2 | 12/2003 | Ginn |
| 6,676,685 B2 | 1/2004 | Pedros et al. |
| 6,682,489 B2 | 1/2004 | Tenerz et al. |
| 6,699,263 B2 | 3/2004 | Cope |
| 6,712,836 B1 | 3/2004 | Berg et al. |
| 6,712,837 B2 | 3/2004 | Akerfeldt et al. |
| 6,749,621 B2 | 6/2004 | Pantages et al. |
| 6,749,622 B2 | 6/2004 | McGuckin, Jr. et al. |
| 6,764,500 B1 | 7/2004 | Muijs van de Moer et al. |
| 6,766,186 B1 | 7/2004 | Hoyns et al. |
| 6,786,915 B2 | 9/2004 | Akerfeldt et al. |
| 6,790,220 B2 | 9/2004 | Morris |
| 6,846,316 B2 | 1/2005 | Abrams |
| 6,855,153 B2 | 2/2005 | Saadat |
| 6,860,895 B1 | 3/2005 | Akerfeldt et al. |
| 6,863,680 B2 | 3/2005 | Ashby |
| 6,909,130 B2 | 6/2005 | Yoda et al. |
| 6,929,655 B2 | 8/2005 | Egnelov |
| 6,932,835 B2 | 8/2005 | Bonutti et al. |
| 6,939,363 B2 | 9/2005 | Akerfeldt |
| 6,949,107 B2 | 9/2005 | McGuckin, Jr. et al. |
| 6,960,224 B2 | 11/2005 | Marino et al. |
| 6,972,027 B2 | 12/2005 | Fallin et al. |
| 6,984,219 B2 | 1/2006 | Ashby |
| 6,997,940 B2 | 2/2006 | Bonutti |
| 7,008,440 B2 | 3/2006 | Sing et al. |
| 7,008,442 B2 | 3/2006 | Brightbill |
| 7,025,756 B2 | 4/2006 | Frazier et al. |
| 7,025,776 B1 | 4/2006 | Houser et al. |
| 7,033,380 B2 | 4/2006 | Schwartz et al. |
| 7,033,393 B2 | 4/2006 | Gainor et al. |
| 7,048,748 B1 | 5/2006 | Ustuner |
| 7,048,755 B2 | 5/2006 | Bonutti et al. |
| 7,083,635 B2 | 8/2006 | Glinn |
| 7,087,073 B2 | 8/2006 | Bonutti |
| 7,094,209 B2 | 8/2006 | Egnelöv |
| 7,115,110 B2 | 10/2006 | Frazier et al. |
| 7,135,032 B2 | 11/2006 | Akerfeldt |
| 7,147,652 B2 | 12/2006 | Bonutti et al. |
| 7,150,757 B2* | 12/2006 | Fallin ............... A61B 17/0487 24/129 R |
| 7,153,323 B1 | 12/2006 | Teoh et al. |
| 7,169,168 B2 | 1/2007 | Muijs Van de Moer et al. |
| 7,175,648 B2 | 2/2007 | Nakao |
| 7,235,091 B2 | 6/2007 | Thornes |
| 7,267,679 B2 | 9/2007 | McGuckin, Jr. et al. |
| 7,285,097 B2 | 10/2007 | Tenerz |
| 7,288,105 B2 | 10/2007 | Oman et al. |
| 7,316,706 B2 | 1/2008 | Bloom et al. |
| 7,329,270 B2 | 2/2008 | Akerfeldt |
| 7,341,595 B2 | 3/2008 | Hinchliffe et al. |
| 7,361,183 B2 | 4/2008 | Ginn |
| 7,468,068 B2 | 12/2008 | Kolster |
| 7,488,340 B2 | 2/2009 | Kauphusman et al. |
| 7,530,990 B2 | 5/2009 | Perriello et al. |
| 7,566,339 B2 | 7/2009 | Fallin et al. |
| 7,582,105 B2 | 9/2009 | Kolster |
| 7,594,923 B2 | 9/2009 | Fallin et al. |
| 7,597,705 B2 | 10/2009 | Forsberg et al. |
| 7,618,435 B2 | 11/2009 | Opolski |
| 7,618,438 B2 | 11/2009 | White et al. |
| 7,621,937 B2 | 11/2009 | Pipenhagenet et al. |
| 7,625,352 B1 | 12/2009 | Ashby et al. |
| 7,637,921 B2 | 12/2009 | Akerfeldt |
| 7,654,963 B2 | 2/2010 | Egnelöv |
| 7,658,751 B2 | 2/2010 | Stone et al. |
| 7,662,160 B2 | 2/2010 | Bojarski et al. |
| 7,662,161 B2 | 2/2010 | Briganti et al. |
| 7,666,199 B2 | 2/2010 | McIntyre |
| 7,717,929 B2 | 5/2010 | Fallman |
| 7,736,378 B2 | 6/2010 | Maahs et al. |
| 7,758,594 B2 | 7/2010 | Lamson et al. |
| 7,775,988 B2 | 8/2010 | Pijls |
| 7,780,699 B2 | 8/2010 | Zhu |
| 7,824,417 B2 | 11/2010 | Magnusson |
| 7,846,180 B2* | 12/2010 | Cerier ............... A61B 17/0057 606/232 |
| 7,862,584 B2* | 1/2011 | Lyons ............... A61B 17/0487 606/232 |
| 7,931,670 B2 | 4/2011 | Fiehler |
| 7,931,671 B2 | 4/2011 | Tenerz |
| 7,938,846 B2 | 5/2011 | Akerfeldt |
| 7,967,840 B2 | 6/2011 | Chanduszko |
| 8,016,857 B2 | 9/2011 | Sater |
| 8,088,143 B2 | 1/2012 | Akerfeldt |
| 8,105,352 B2 | 1/2012 | Egnelov |
| 8,109,968 B2* | 2/2012 | Ashley ............... A61B 17/0487 24/130 |
| 8,118,831 B2 | 2/2012 | Egnelov |
| 8,118,832 B1 | 2/2012 | Morris |
| 8,118,833 B2 | 2/2012 | Seibold |
| 8,267,959 B2 | 9/2012 | Fallman |
| 8,308,762 B2 | 11/2012 | Mahlin |

(56) References Cited

U.S. PATENT DOCUMENTS

| | | | |
|---|---|---|---|
| 8,348,971 B2 | 1/2013 | Khanna et al. |
| 8,382,793 B2 | 2/2013 | Egnelöv |
| 8,398,675 B2 | 3/2013 | Egnelöv |
| 8,444,673 B2 | 5/2013 | Thielen et al. |
| RE44,297 E | 6/2013 | Akerfeldt |
| 8,469,944 B2 | 6/2013 | Mahlin |
| 8,480,686 B2 | 7/2013 | Bakos |
| 8,647,365 B2 | 2/2014 | Tegels |
| 8,652,166 B2 | 2/2014 | Akerfeldt |
| 8,663,254 B2 | 3/2014 | Feussner |
| 2001/0010005 A1 | 7/2001 | Kammerer |
| 2002/0055767 A1 | 5/2002 | Forde |
| 2002/0082622 A1 | 6/2002 | Kane |
| 2002/0095179 A1 | 7/2002 | Tenerz et al. |
| 2002/0165561 A1 | 11/2002 | Ainsworth et al. |
| 2002/0165572 A1 | 11/2002 | Saadat |
| 2003/0009180 A1 | 1/2003 | Hinchliffe et al. |
| 2003/0050665 A1 | 3/2003 | Ginn |
| 2003/0055451 A1 | 3/2003 | Jones et al. |
| 2003/0088256 A1 | 5/2003 | Conston et al. |
| 2003/0088269 A1 | 5/2003 | Ashby |
| 2003/0105487 A1 | 6/2003 | Benz et al. |
| 2003/0130694 A1 | 7/2003 | Bojarski et al. |
| 2003/0144695 A1 | 7/2003 | McGuckin, Jr. et al. |
| 2003/0187473 A1 | 10/2003 | Berenstein et al. |
| 2003/0191495 A1 | 10/2003 | Ryan et al. |
| 2004/0002764 A1 | 1/2004 | Gainer et al. |
| 2004/0010287 A1 | 1/2004 | Bonutti |
| 2004/0039413 A1 | 2/2004 | Akerfeldt |
| 2004/0049207 A1 | 3/2004 | Goldfarb |
| 2004/0093025 A1 | 5/2004 | Egnelov |
| 2004/0133236 A1 | 7/2004 | Chanduszko |
| 2004/0133238 A1 | 7/2004 | Cerier |
| 2004/0143294 A1 | 7/2004 | Corcoran et al. |
| 2004/0153103 A1 | 8/2004 | Schwartz et al. |
| 2004/0158287 A1 | 8/2004 | Cragg et al. |
| 2004/0176800 A1 | 9/2004 | Paraschac et al. |
| 2004/0230223 A1 | 11/2004 | Bonutti et al. |
| 2005/0033326 A1 | 2/2005 | Briganti |
| 2005/0059982 A1 | 3/2005 | Zung et al. |
| 2005/0065547 A1 | 3/2005 | Marino et al. |
| 2005/0070957 A1 | 3/2005 | Das |
| 2005/0075654 A1 | 4/2005 | Kelleher |
| 2005/0085852 A1 | 4/2005 | Ditter |
| 2005/0085855 A1 | 4/2005 | Forsberg |
| 2005/0090859 A1 | 4/2005 | Ravlkumar |
| 2005/0096696 A1 | 5/2005 | Forsberg |
| 2005/0096697 A1 | 5/2005 | Forsberg et al. |
| 2005/0107807 A1 | 5/2005 | Nakao |
| 2005/0125030 A1 | 6/2005 | Forsberg et al. |
| 2005/0125031 A1 | 6/2005 | Pipenhagen et al. |
| 2005/0125032 A1 | 6/2005 | Whisenant et al. |
| 2005/0169974 A1 | 8/2005 | Tenerz et al. |
| 2005/0177182 A1 | 8/2005 | van der Burg et al. |
| 2005/0192627 A1 | 9/2005 | Whisenant et al. |
| 2005/0192630 A1 | 9/2005 | Maas et al. |
| 2005/0216059 A1* | 9/2005 | Bonutti ............ A61B 17/0487 606/232 |
| 2005/0267524 A1 | 12/2005 | Chanduszko |
| 2005/0283193 A1 | 12/2005 | Tullberg et al. |
| 2005/0288786 A1 | 12/2005 | Chanduszko |
| 2006/0069408 A1 | 3/2006 | Kato |
| 2006/0100665 A1 | 5/2006 | Von Oepen et al. |
| 2006/0106418 A1 | 5/2006 | Seibold et al. |
| 2006/0135991 A1 | 6/2006 | Kawaura |
| 2006/0142797 A1 | 6/2006 | Egnelov |
| 2006/0155327 A1 | 7/2006 | Briganti |
| 2006/0167495 A1 | 7/2006 | Bonutti et al. |
| 2006/0173492 A1 | 8/2006 | Akerfeldt et al. |
| 2006/0212073 A1 | 9/2006 | Bonutti et al. |
| 2006/0217760 A1 | 9/2006 | Widomski et al. |
| 2006/0217765 A1 | 9/2006 | Bonutti et al. |
| 2006/0241695 A1 | 10/2006 | Bonutti et al. |
| 2006/0265009 A1 | 11/2006 | Bonutti |
| 2006/0271105 A1 | 11/2006 | Foerster et al. |
| 2006/0276871 A1 | 12/2006 | Lamson et al. |
| 2007/0010851 A1 | 1/2007 | Chanduszko |
| 2007/0010857 A1 | 1/2007 | Sugimoto et al. |
| 2007/0060858 A1 | 3/2007 | Sogard et al. |
| 2007/0073322 A1 | 3/2007 | Mikkaichi et al. |
| 2007/0073337 A1 | 3/2007 | Abbott |
| 2007/0088388 A1 | 4/2007 | Opolski |
| 2007/0135826 A1 | 6/2007 | Zaver |
| 2007/0149987 A1 | 6/2007 | Wellman et al. |
| 2007/0149998 A1 | 6/2007 | Wicks et al. |
| 2007/0149999 A1 | 6/2007 | Szabo et al. |
| 2007/0150002 A1 | 6/2007 | Szabo et al. |
| 2007/0156175 A1* | 7/2007 | Weadock ............ A61B 17/0401 606/216 |
| 2007/0185529 A1 | 8/2007 | Coleman |
| 2007/0185532 A1 | 8/2007 | Stone et al. |
| 2007/0198038 A1 | 8/2007 | Cohen |
| 2007/0239208 A1 | 10/2007 | Crawford |
| 2007/0239209 A1 | 10/2007 | Fallman |
| 2007/0244518 A1 | 10/2007 | Callaghan |
| 2007/0255316 A1 | 11/2007 | McIntyre |
| 2007/0276437 A1* | 11/2007 | Call .................. A61B 17/0487 606/232 |
| 2008/0071310 A1 | 3/2008 | Hoffman et al. |
| 2008/0082128 A1 | 4/2008 | Stone |
| 2008/0114395 A1 | 5/2008 | Mathisen |
| 2008/0140092 A1 | 6/2008 | Stone et al. |
| 2008/0243182 A1 | 10/2008 | Bates |
| 2009/0030450 A1 | 1/2009 | Preinitz et al. |
| 2009/0036919 A1 | 2/2009 | Preinitz et al. |
| 2009/0036920 A1 | 2/2009 | Preinitz et al. |
| 2009/0043333 A1 | 2/2009 | Preinitz et al. |
| 2009/0076541 A1 | 3/2009 | Chin |
| 2009/0088778 A1 | 4/2009 | Miyamoto |
| 2009/0163934 A1 | 6/2009 | Raschdorf, Jr. |
| 2009/0177225 A1 | 7/2009 | Nunez et al. |
| 2009/0210004 A1 | 8/2009 | McGuckin, Jr. et al. |
| 2009/0216267 A1 | 8/2009 | Willard |
| 2009/0234377 A1 | 9/2009 | Mahlin et al. |
| 2009/0248064 A1 | 10/2009 | Preinitz |
| 2009/0326460 A1 | 12/2009 | Beardsley |
| 2010/0114156 A1 | 5/2010 | Mehl |
| 2010/0312224 A1 | 12/2010 | Atthoff et al. |
| 2011/0071551 A1 | 3/2011 | Singhatat |
| 2011/0082495 A1 | 4/2011 | Ruiz |
| 2011/0270307 A1 | 11/2011 | Szabo |
| 2012/0078294 A1 | 3/2012 | Tarmin et al. |

FOREIGN PATENT DOCUMENTS

| | | |
|---|---|---|
| EP | 0920842 | 6/1999 |
| EP | 1671591 | 6/2006 |
| EP | 1671592 | 6/2006 |
| EP | 2055236 | 5/2009 |
| EP | 2294986 | 3/2011 |
| EP | 2412317 | 2/2012 |
| WO | WO 94/28800 | 12/1994 |
| WO | 9520913 | 8/1995 |
| WO | WO 95/32670 | 12/1995 |
| WO | 9707741 | 3/1997 |
| WO | 9827868 | 7/1998 |
| WO | 9900055 | 1/1999 |
| WO | 9905977 | 2/1999 |
| WO | 9938454 | 8/1999 |
| WO | WO 01/40348 | 11/2000 |
| WO | WO 00/78226 | 12/2000 |
| WO | WO 2004012601 | 2/2004 |
| WO | WO 2004/098418 | 11/2004 |
| WO | 2004/112864 | 12/2004 |
| WO | WO 2006/093970 | 9/2006 |

* cited by examiner

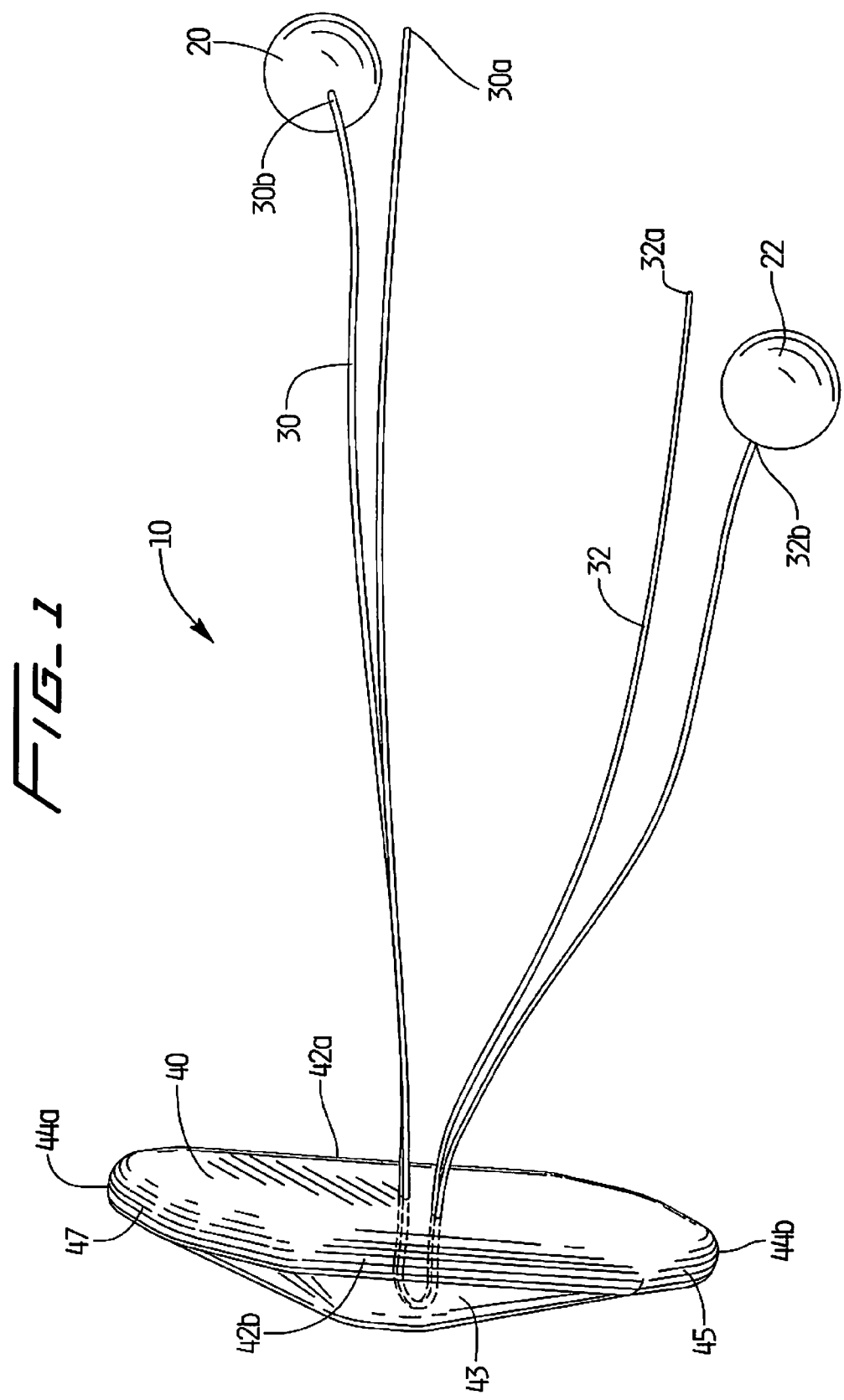

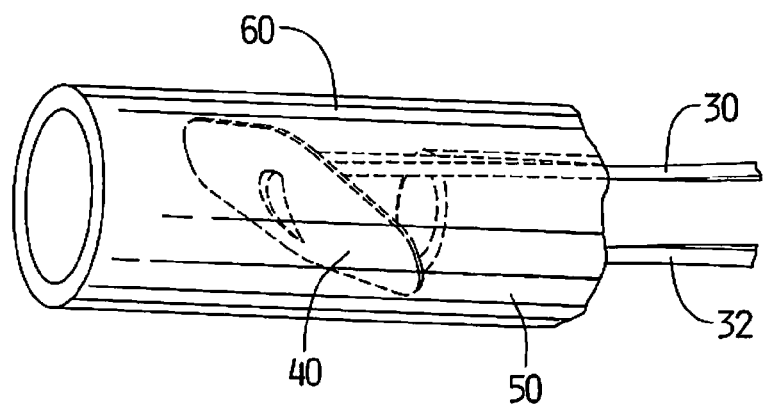
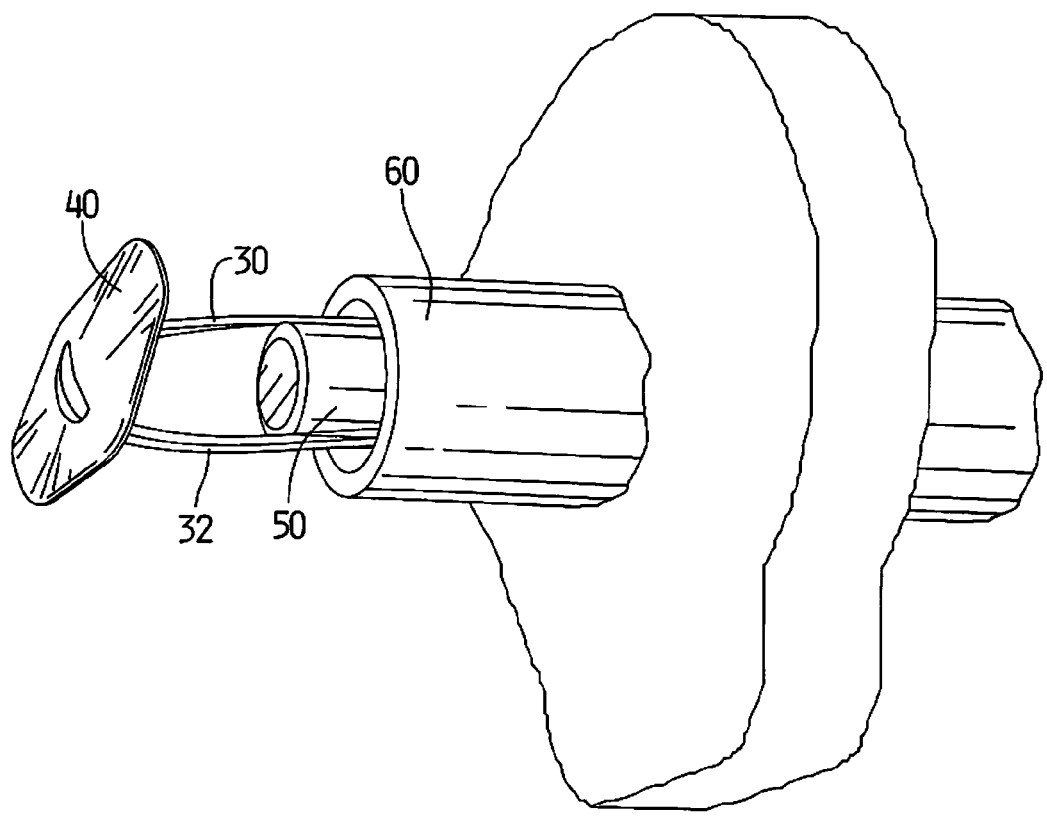

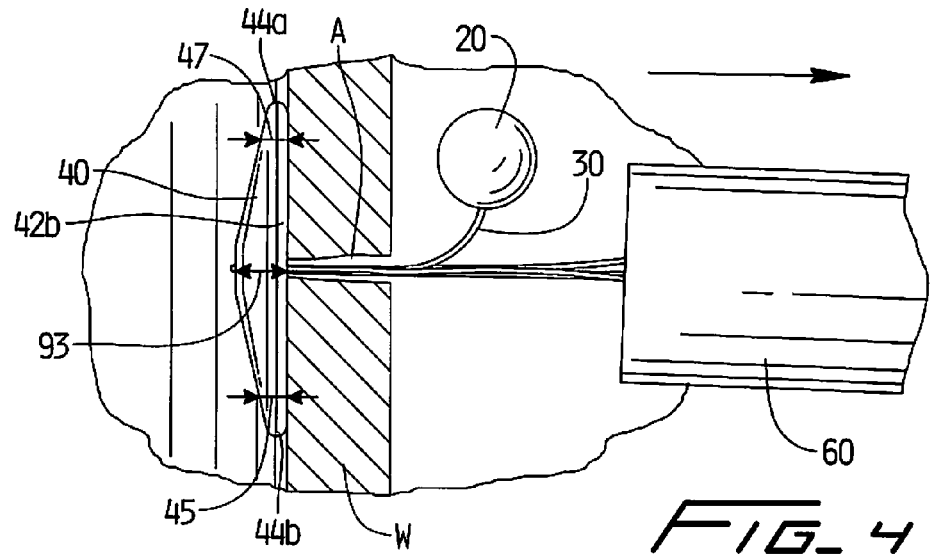
FIG_4
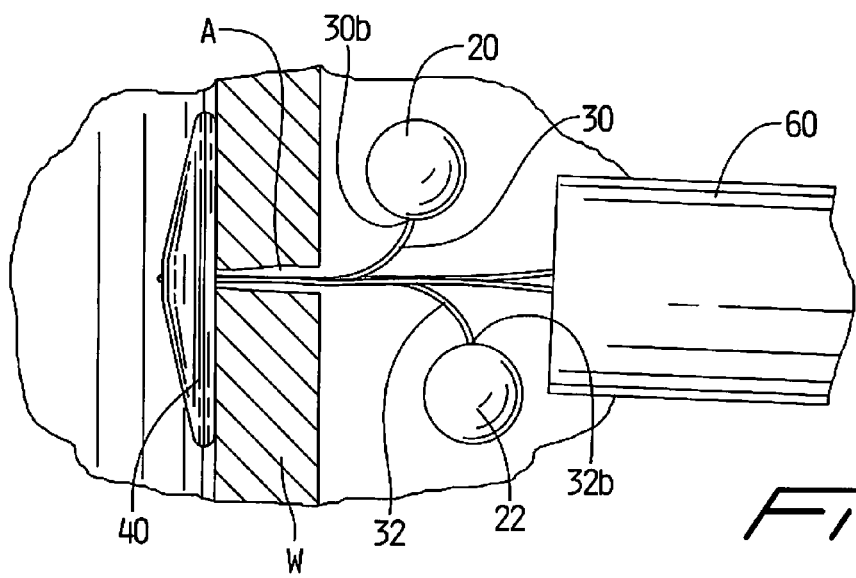
FIG_5
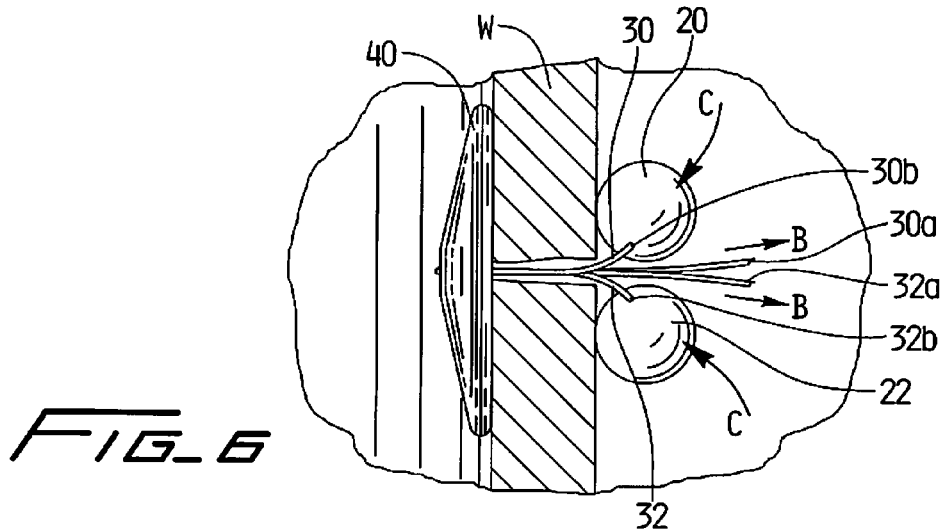
FIG_6

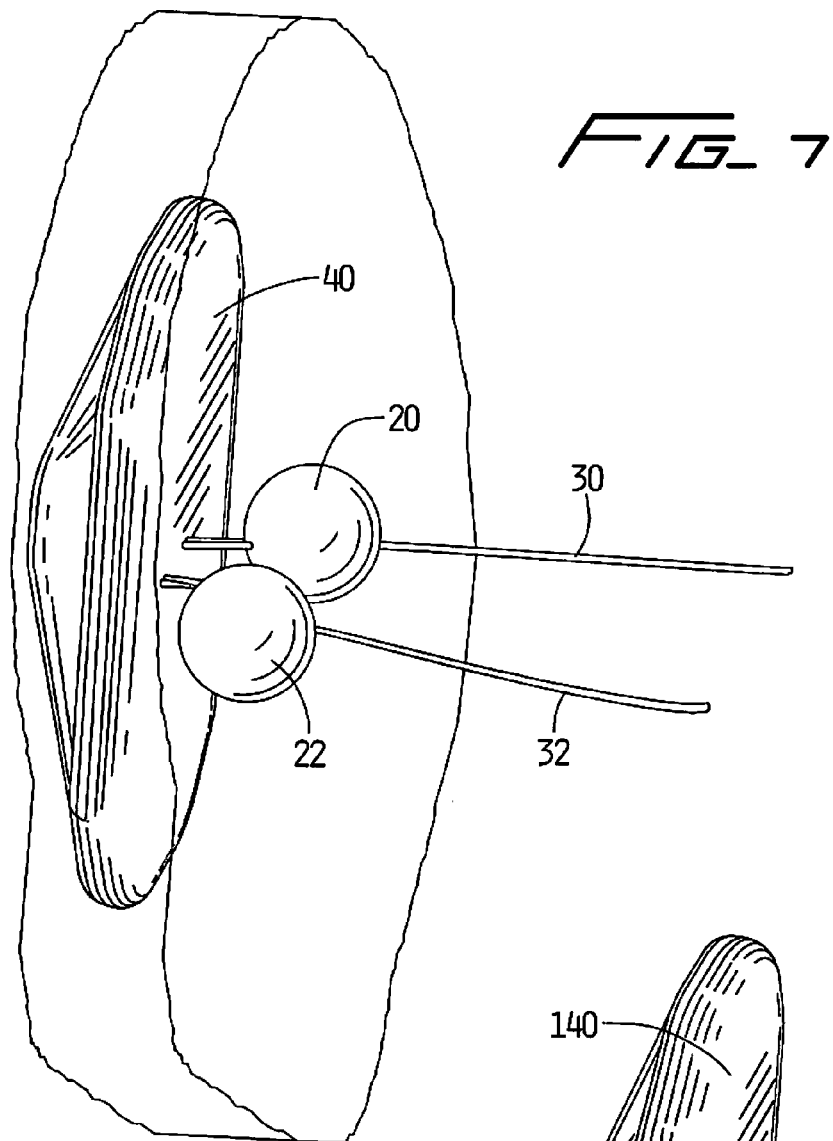
FIG_7
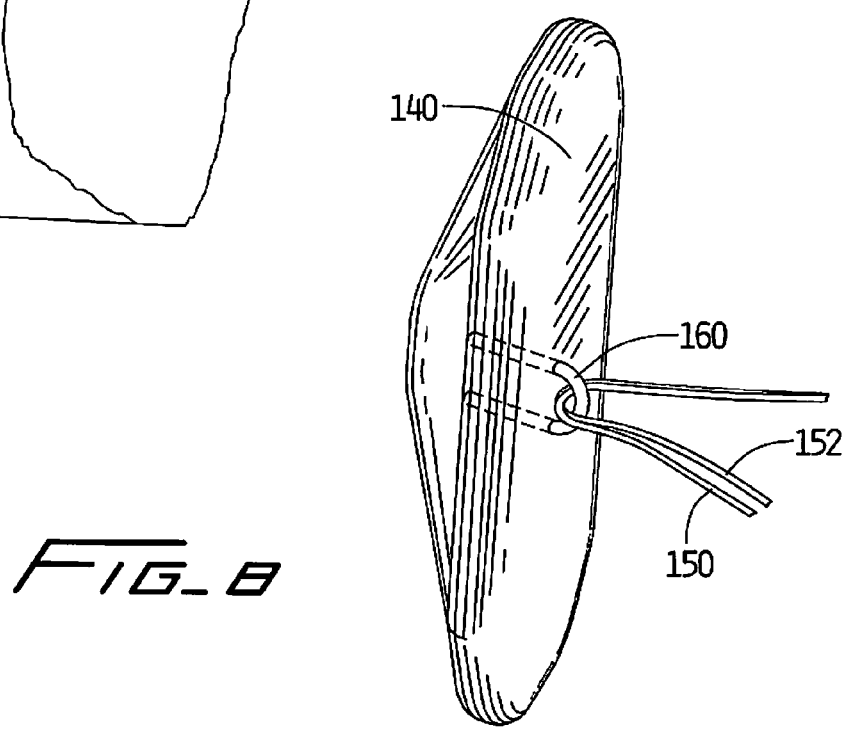
FIG_8

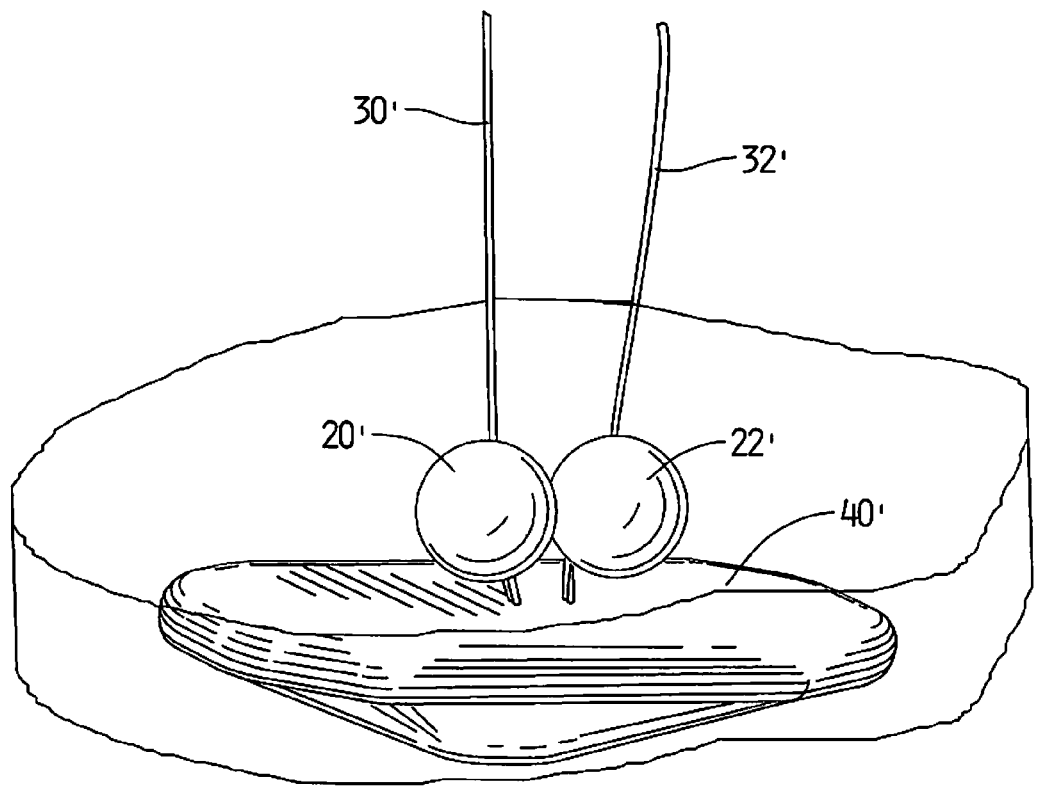

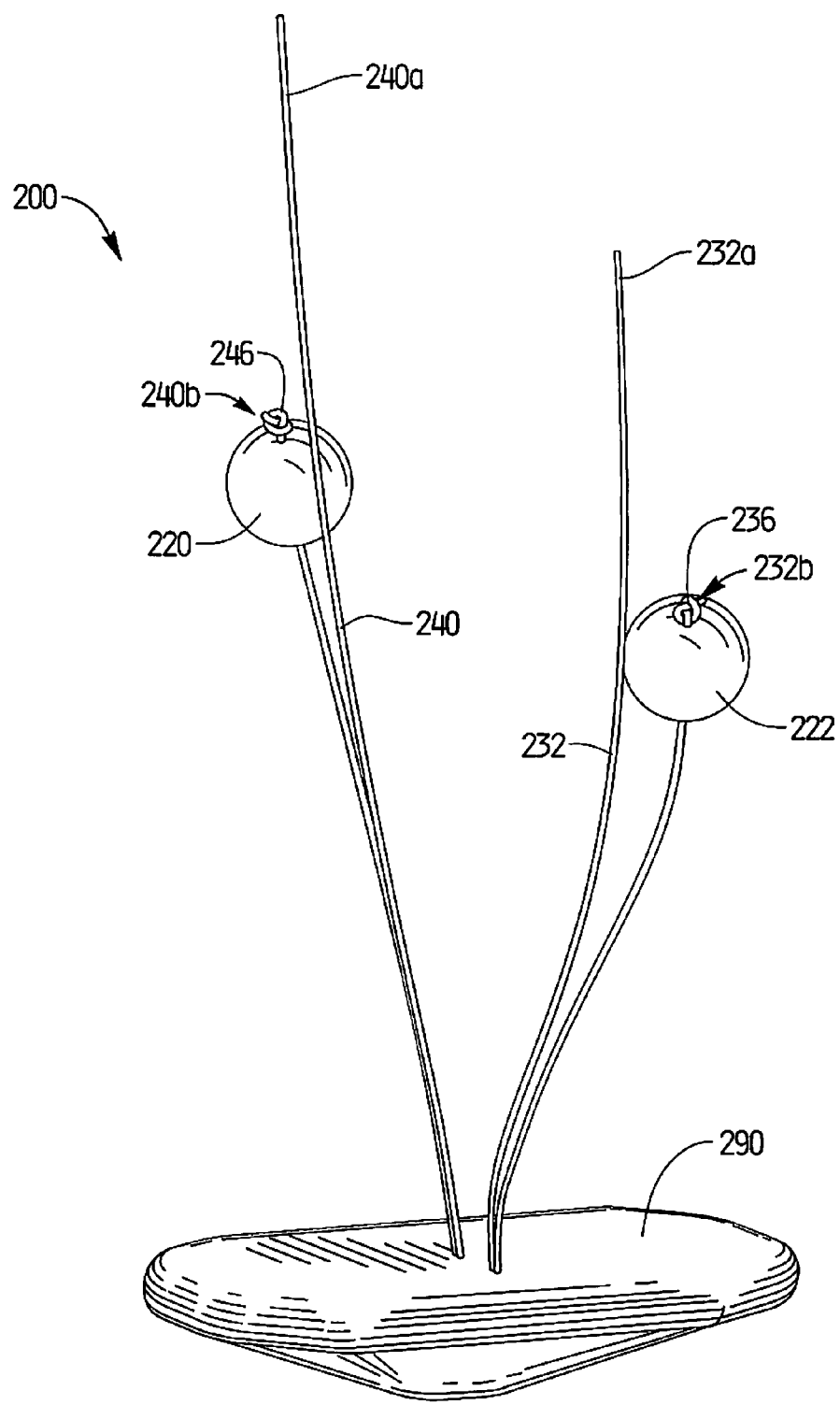
FIG_10

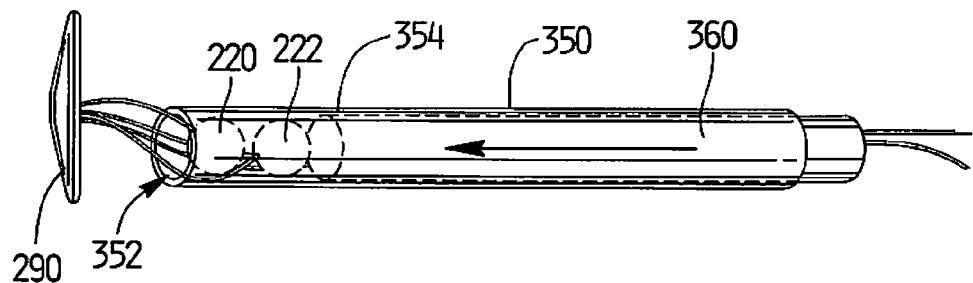
FIG_11
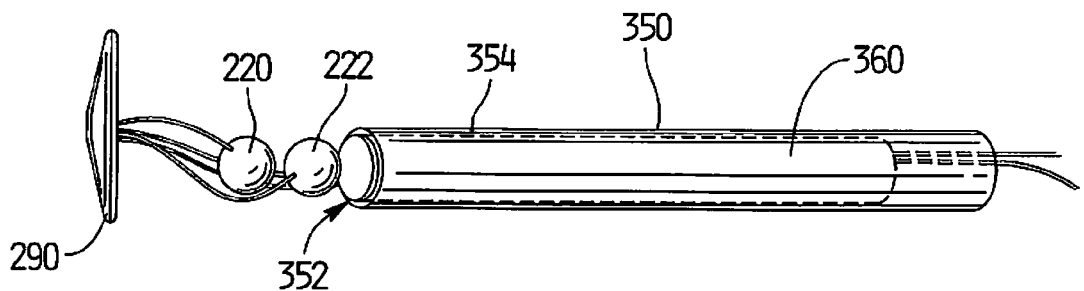
FIG_12
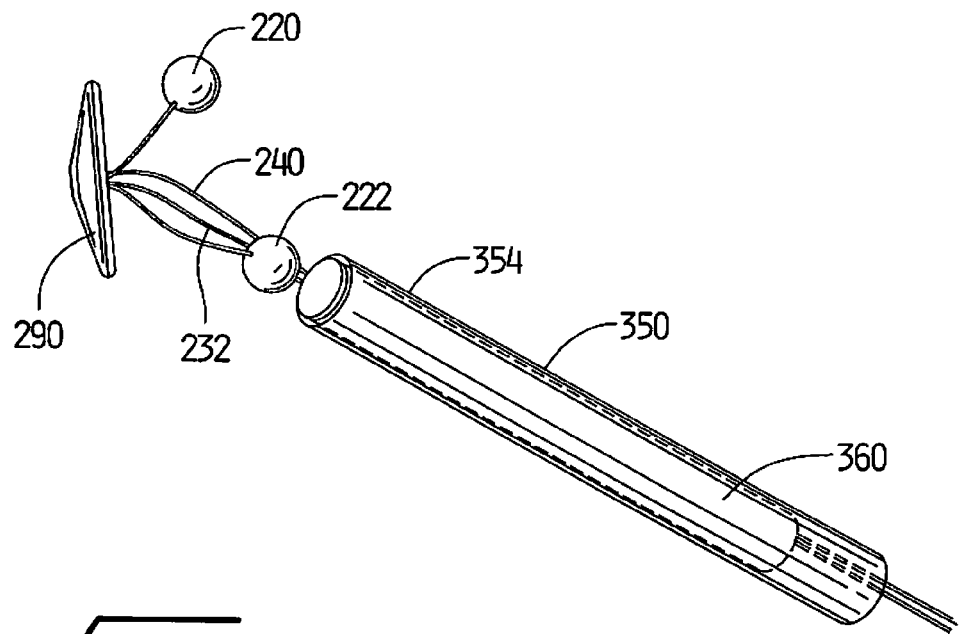
FIG_13A

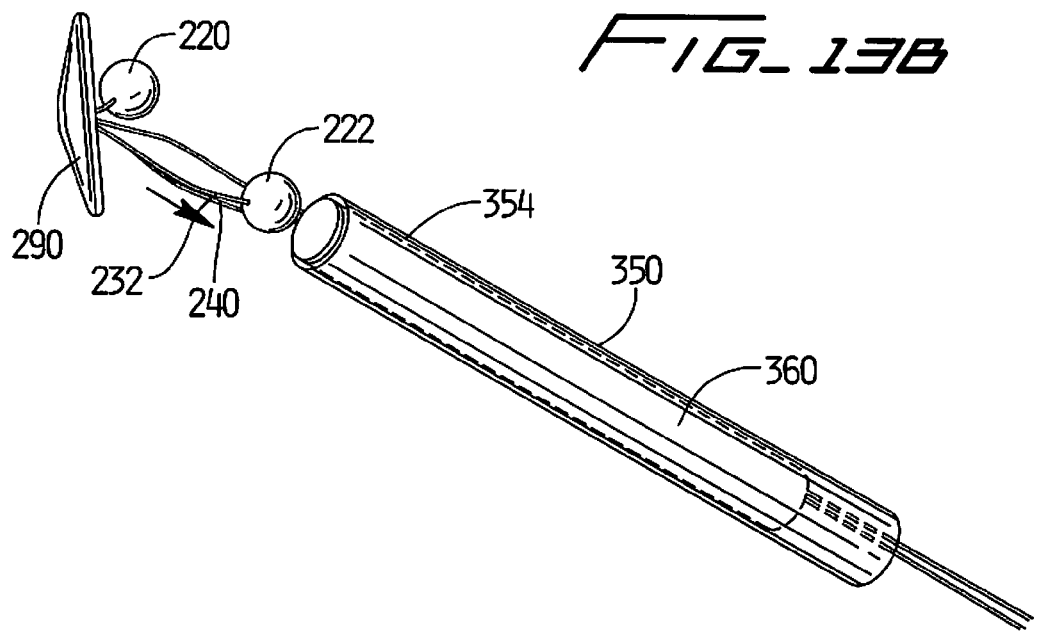
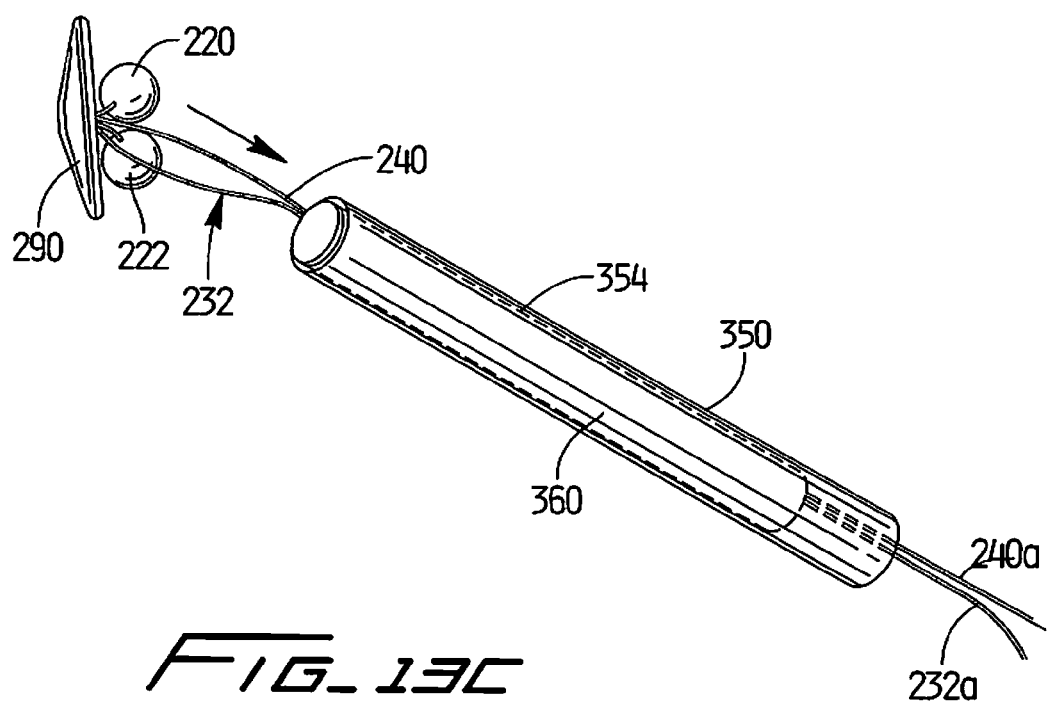

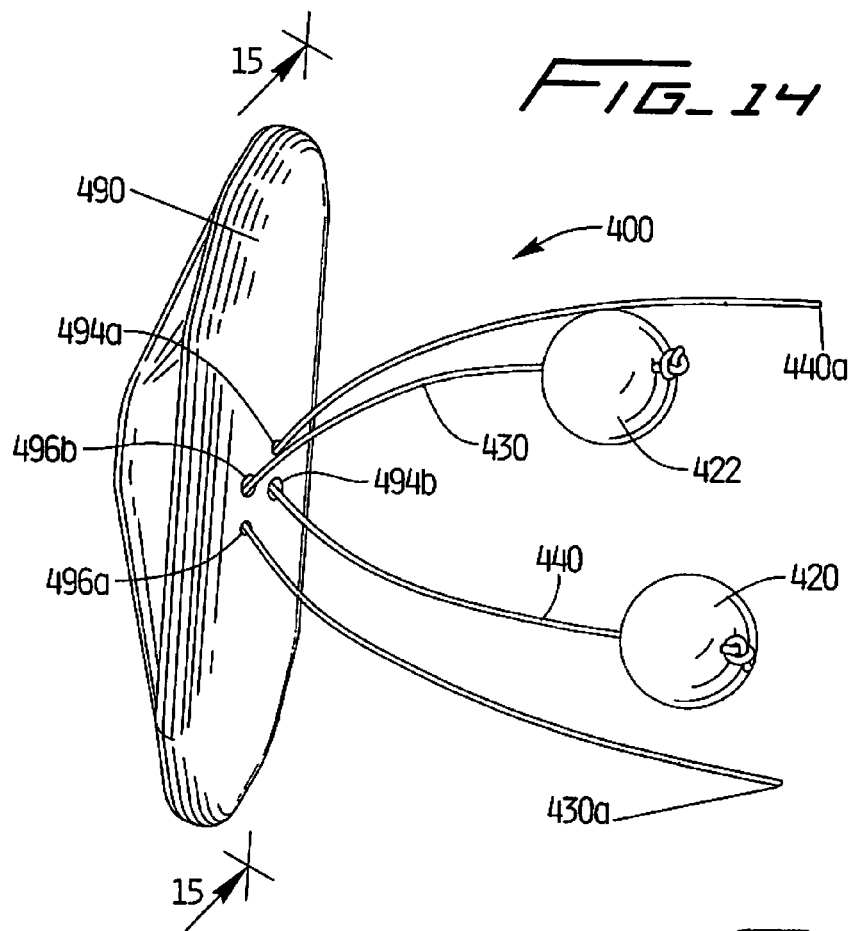
FIG_14
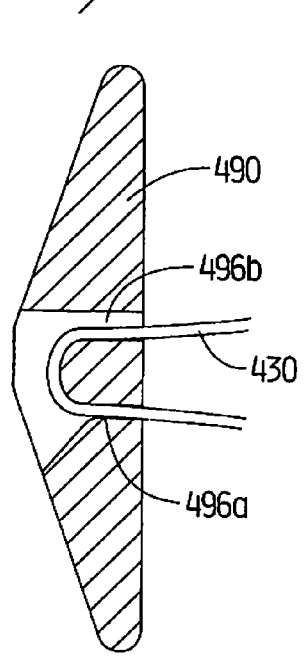
FIG_15
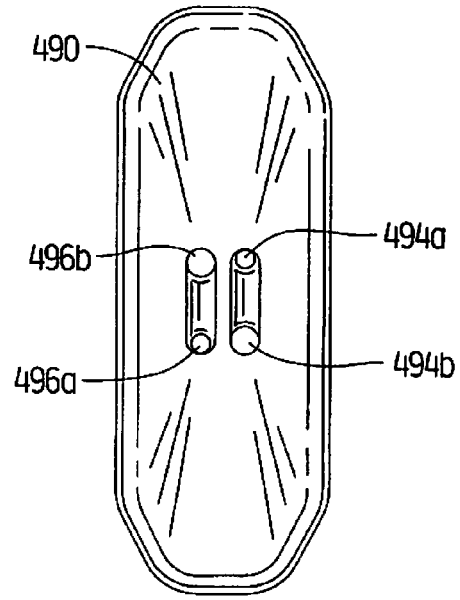
FIG_16

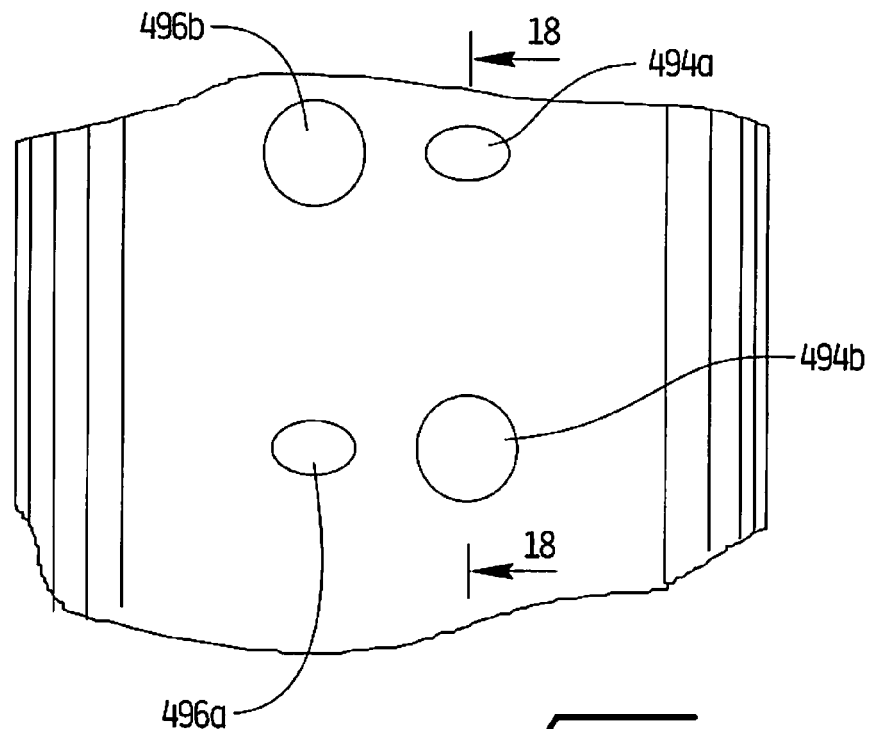
FIG_17
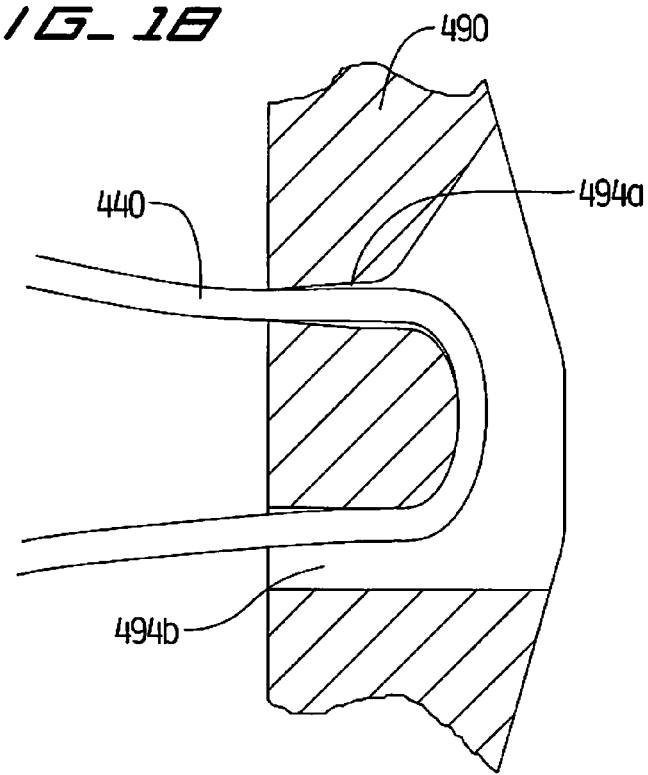
FIG_18

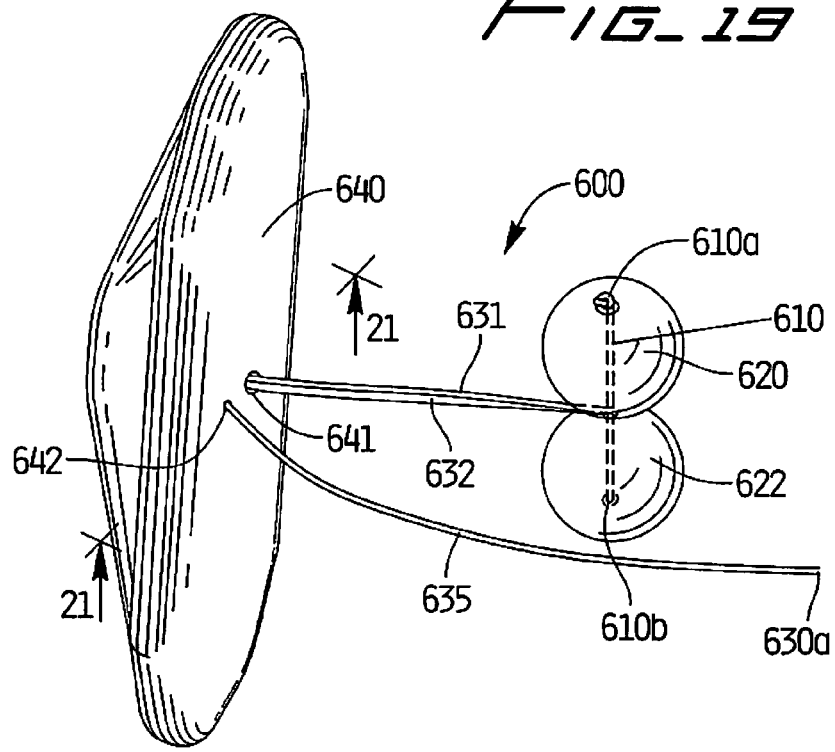
FIG_19
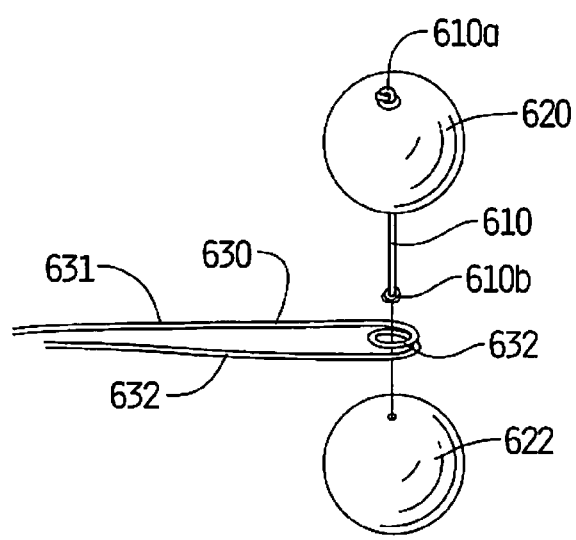
FIG_20
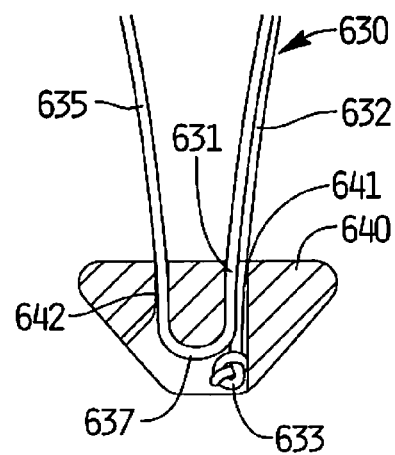
FIG_21

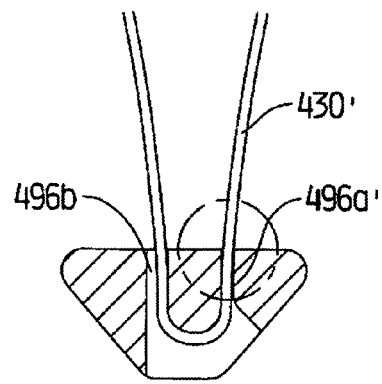
FIG_22
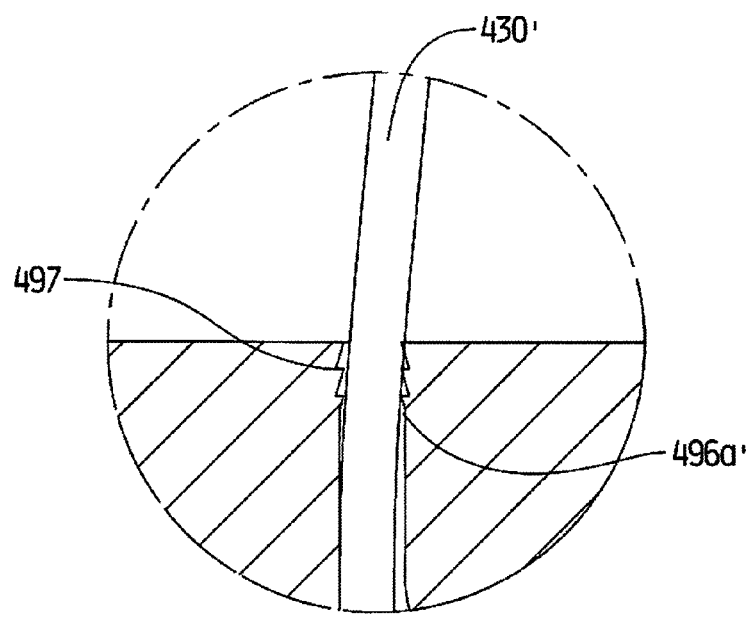
FIG_23

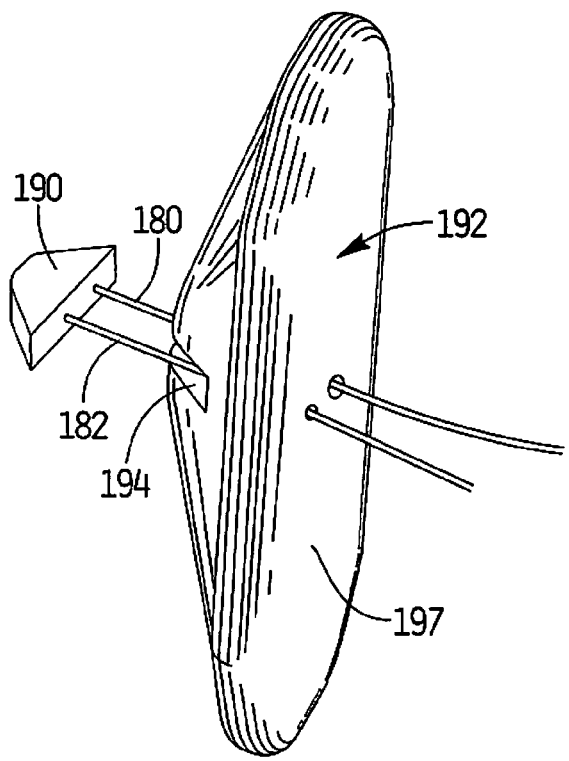
FIG_24
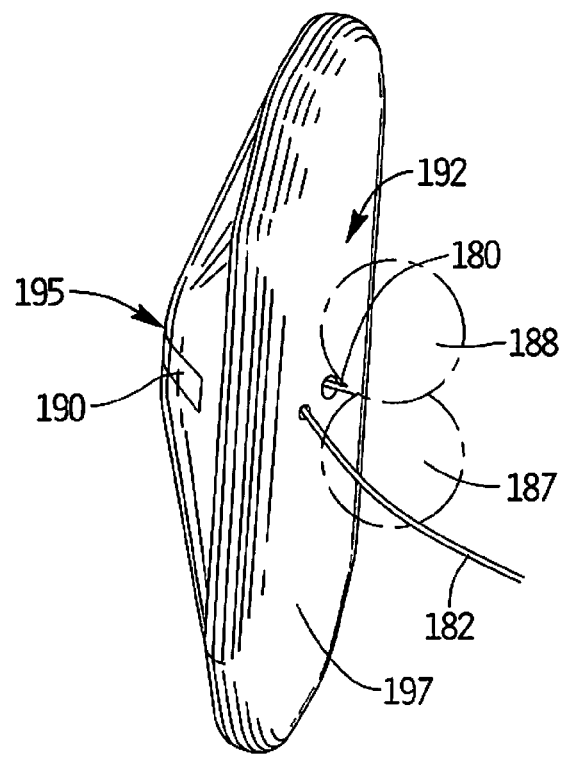
FIG_25

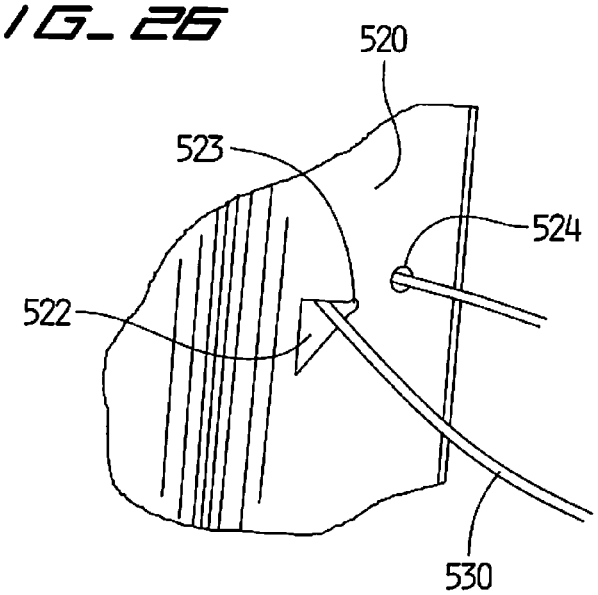
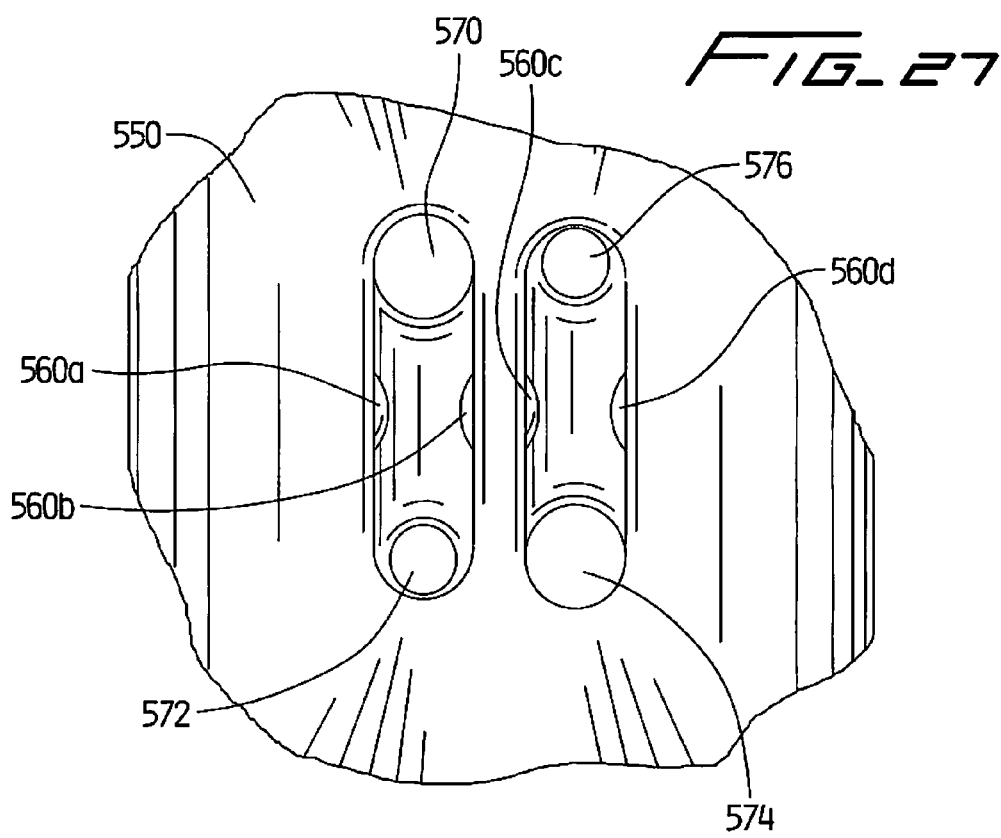

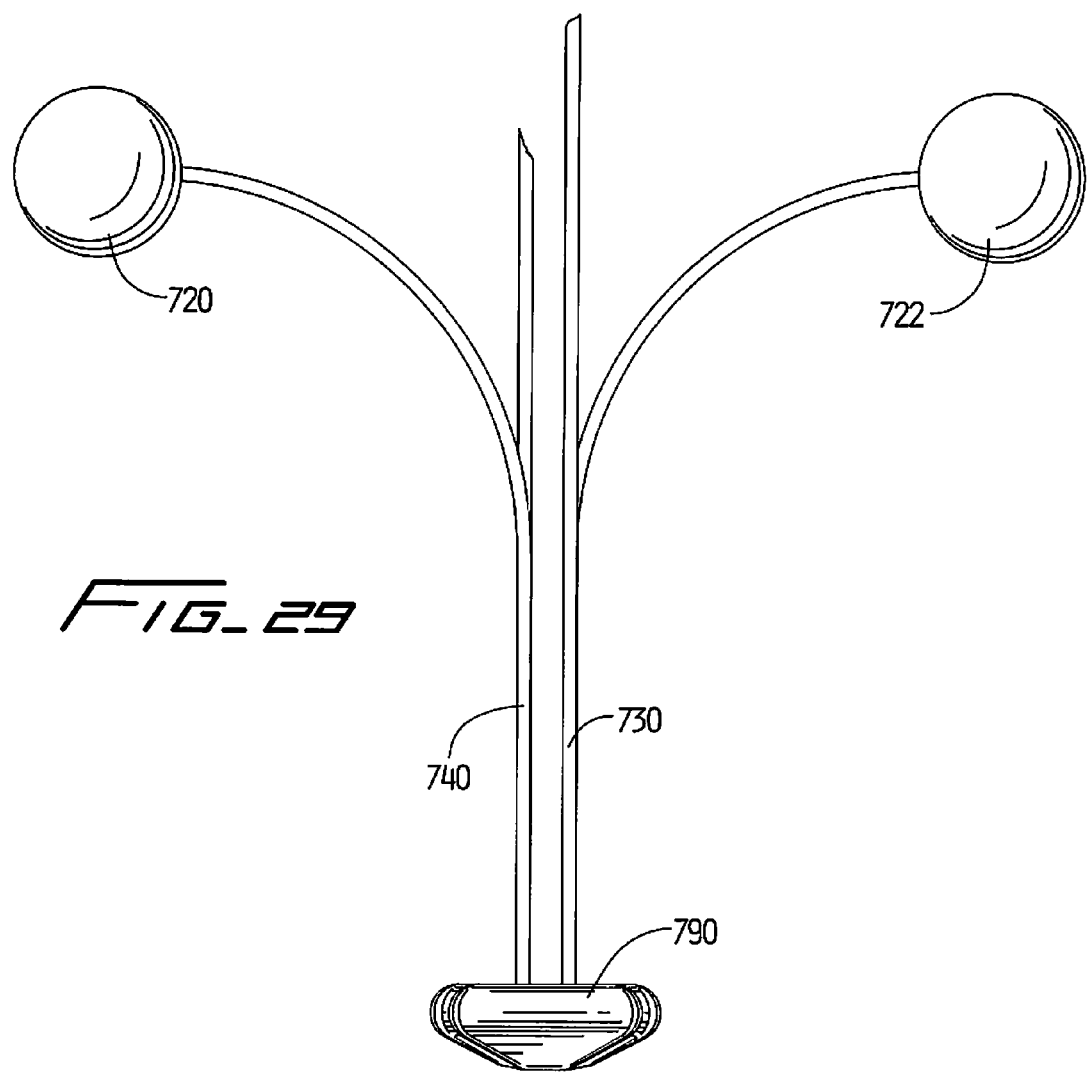
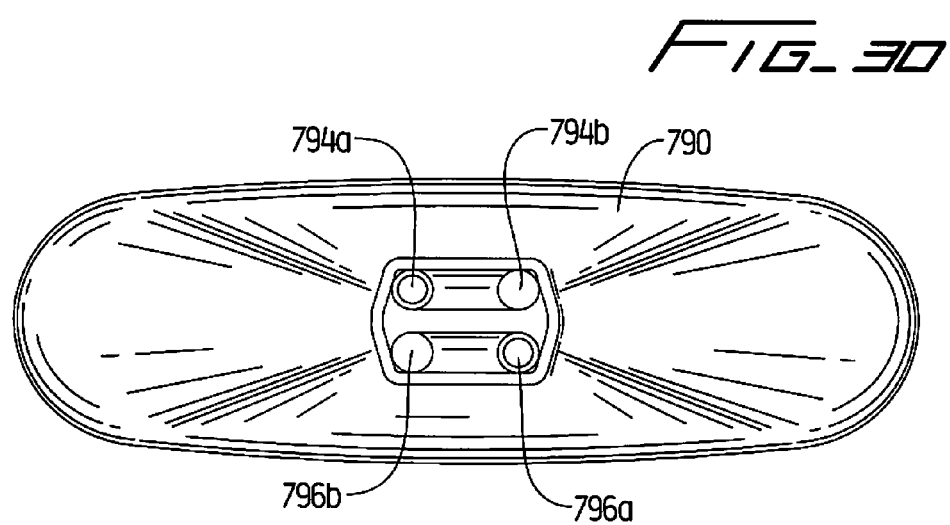

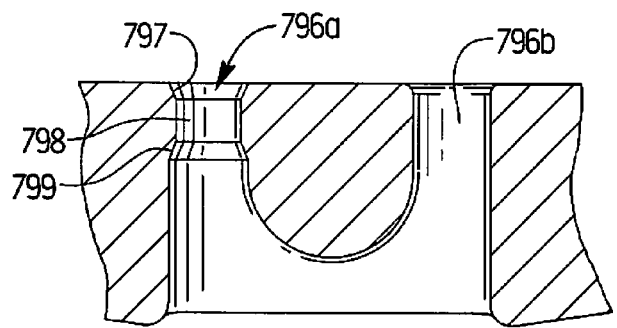
FIG_31
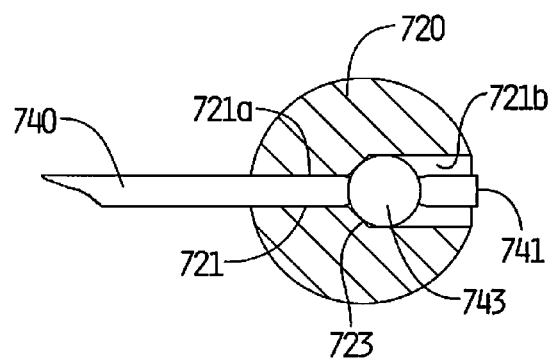
FIG_32
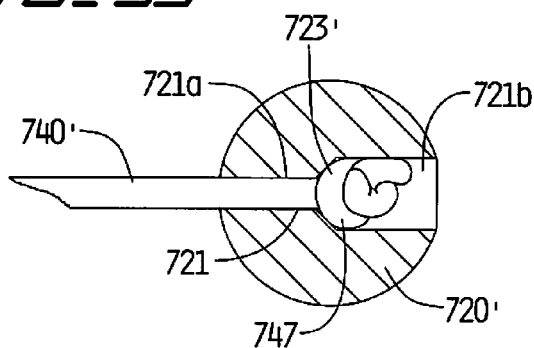
FIG_33
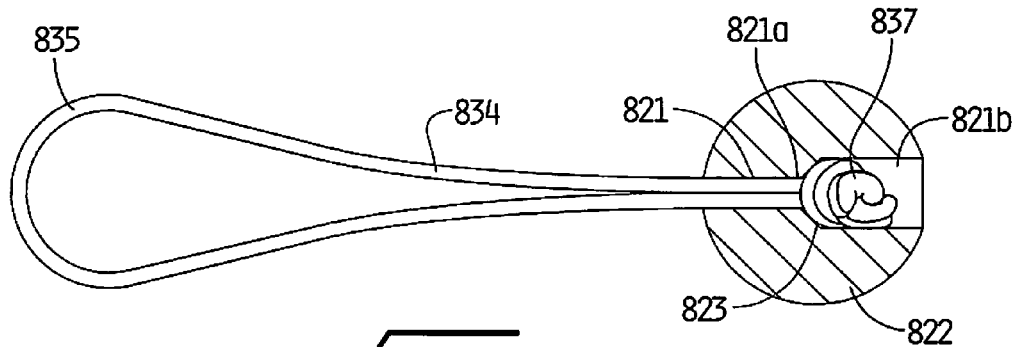
FIG_34

VASCULAR HOLE CLOSURE DEVICE

This application is a continuation of patent application Ser. No. 12/854,988, filed Aug. 12, 2010 which claims priority from provisional application Ser. No. 61/241,555, filed Sep. 11, 2009 and is a continuation in part of application Ser. No. 12/358,411, filed Jan. 23, 2009, now U.S. Pat. No. 8,070,772 which claims priority from provisional application Ser. No. 61/066,072, filed Feb. 15, 2008. The entire contents of each of these applications are incorporated herein by reference.

BACKGROUND

1. Technical Field

This application relates to a vascular device and more particularly to a device for closing openings in vessel walls.

2. Background of Related Art

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery.

Several approaches to date have been used to close femoral access holes. In one approach, manual compression by hand over the puncture site is augmented by a sandbag or weight until the blood coagulates. With this approach, it can take up to six hours for the vessel hole to close and for the patient to be able to ambulate. This inefficiency increases the surgical procedure time as well as the overall cost of the procedure since the hospital staff must physically maintain pressure and the patient's discharge is delayed because of the inability to ambulate.

In another approach to close the vessel puncture site, a clamp is attached to the operating table and the patient's leg. The clamp applies pressure to the vessel opening. The patient, however, must still be monitored to ensure the blood is coagulating, requiring additional time of the hospital staff and increasing the cost of the procedure.

To avoid the foregoing disadvantages of manual pressure approaches, suturing devices have been developed. One such suturing device, sold by Abbott, advances needles adjacent the vessel wall opening and pulls suture material outwardly through the wall adjacent the opening. The surgeon then ties a knot in the suture, closing the opening. One difficulty with the procedure involves the number of steps required by the surgeon to deploy the needles, capture the suture, withdraw the suture, and tie the knot and secure the suture. Moreover, the surgeon cannot easily visualize the suture because of the depth of the femoral artery (relative to the skin) and essentially ties the suture knot blindly or blindly slips a pre-tied knot into position. Additionally, the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system. It is also difficult to pass the needle through calcified vessels.

U.S. Pat. No. 4,744,364 discloses another approach for sealing a vessel puncture in the form of a device having an expandable closure member with a filament for pulling it against the vessel wall. The closure member is held in place by a strip of tape placed on the skin to hold the filament in place. However, the closure device is still subject to movement which can cause leakage through the puncture. Additionally, if the suture becomes loose, the closure member is not retained and can flow downstream in the vessel. Moreover, since the suture extends through the skin, a potential pathway for infection is created. The closure device in U.S. Pat. No. 5,545,178 includes a resorbable collagen foam plug located within the puncture tract. However, since coagulation typically takes up to twenty minutes and blood can leak in between the plug and tissue tract, manual pressure must be applied to the puncture for a period of time, until the collagen plug expands within the tract.

It would therefore be advantageous to provide a device which would more quickly and effectively close openings (punctures) in vessel walls. Such device would advantageously avoid the aforementioned time and expense of applying manual pressure to the opening, simplify the steps required to close the opening, avoid widening of the opening, and more effectively retain the closure device in the vessel.

Commonly assigned U.S. Pat. No. 7,662,161 discloses effective vascular hole closure devices which have the foregoing advantages. It would be further advantageous to provide a vascular hole closure device which is adjustable to accommodate different tissue thicknesses and applies a more constant clamping/retaining force between the intravascular and extravascular components of the device irrespective of tissue thickness.

SUMMARY

The present invention overcomes the disadvantages and deficiencies of the prior art. The present invention provides a device for closing an aperture in a vessel wall, the aperture having an external opening in an external region of the vessel wall and an internal opening in an internal region of the vessel wall. The device comprises a covering member positionable inside the vessel against the internal opening of the aperture and having a dimension to prevent egress of fluid through the aperture and having a first opening. A first retainer is positionable external of the vessel. A flexible connecting member operatively connects the covering member and the first retainer and advances the retainer toward the covering member. The first opening of the covering member is configured to restrict movement of the connecting member.

Preferably the connecting member comprises a first suture and the first retainer is attached to the first suture whereby pulling of the first suture moves the first retainer toward the covering member.

The device may further comprise a second retainer movable toward the covering member by pulling a second suture attached to the second retainer. The covering member can have a second opening configured to restrict movement of the second suture. In preferred embodiments, the first and second retainers are spherical.

In preferred embodiments, the first and second retainers and the first and second sutures are composed of a resorbable material.

In a preferred embodiment, the retainers are positioned in a substantially side by side relationship in a placement position and are positioned in a stacked relationship in a delivery position.

In one embodiment, the opening has a dimension to frictionally engage the connecting member. In another embodiment, the opening includes a plurality of teeth to retain the connecting member.

The covering member is preferably pivotable between a longitudinal orientation for delivery and a transverse position for placement The device may include a third opening for unrestricted movement of the first suture and fourth opening for unrestricted movement of the second suture.

In another aspect, the present disclosure provides a method of closing an aperture in a vessel wall, the aperture having an external opening in an external region of the vessel wall and an internal opening in an internal region of the vessel wall. The method comprises the steps of:
  inserting a covering member inside the vessel against the internal opening of the aperture, the covering member having a dimension to prevent egress of fluid through the aperture and having a connecting member extending therefrom;
  inserting a first retainer external of the vessel; and
  applying a sufficient force to overcome resistance to movement of the connecting member to advance the first retainer toward the covering member.

In one embodiment, the step of advancing the first retainer comprises the step of moving a suture attached to the first retainer through an opening in the covering member having a diameter substantially the same as the outer diameter of the suture. The method preferably includes the steps of inserting a second retainer external of the vessel and advancing the second retainer toward the covering member by pulling a second suture connected to the second retainer.

In one embodiment, the step of advancing the first retainer comprises the step of moving a first suture attached to the first retainer through an opening having a plurality of teeth engagable with the outer surface of the suture. In another embodiment, the step of advancing the first retainer comprises the step of moving a first suture attached to the first retainer between bumps on the covering member.

BRIEF DESCRIPTION OF THE DRAWINGS

Preferred embodiment(s) of the present disclosure are described herein with reference to the drawings wherein:

FIG. 1 is a perspective view of a first embodiment of the closure device of the present invention;

FIG. 2 is a side perspective view of the covering (blocking) member of the closure device of FIG. 1 shown within a delivery sheath;

FIG. 3 is a side perspective view illustrating the covering member of FIG. 2 deployed from the delivery sheath;

FIG. 4 is a side view illustrating one of the spherical retainers of the closure device deployed from the sheath (the vessel wall shown in cross-section);

FIG. 5 illustrates both spherical retainers deployed from the sheath;

FIG. 6 illustrates the sutures pulled to move the spherical retainers toward the covering member for positioning in a side by side relationship against the outer surface of the vessel wall;

FIG. 7 is a perspective view illustrating the retainers in the placement position;

FIG. 8 is a perspective view of the covering member and sutures of an alternate embodiment of the closure device of the present invention showing the sutures attached to the covering member via a looped suture;

FIG. 9 is a perspective view illustrating an alternate orientation of the retainers in the placement position;

FIG. 10 is a perspective view of another alternate embodiment of the closure device of the present invention;

FIGS. 11-13C illustrate schematically the steps of insertion of the closure device of FIG. 10 (the delivery sheath not shown for clarity) wherein:

FIG. 11 illustrates the covering member distal of the retainer tube and the retainers inside the retainer tube;

FIG. 12 illustrates the retainers advanced from the retainer tube;

FIG. 13A illustrates the first retainer being advanced towards the covering member;

FIG. 13B illustrates the first retainer further advanced toward the covering member;

FIG. 13C illustrates the second retainer advanced toward the covering member;

FIG. 14 is a perspective of yet another alternate embodiment of the closure device of the present invention;

FIG. 15 is a cross-sectional view taken along lines 15-15 of FIG. 14;

FIG. 16 is a bottom view of the covering member of FIG. 14;

FIG. 17 is a top view of a portion of the covering member of FIG. 14 with the suture removed for clarity;

FIG. 18 is a cross-sectional view taken along lines 18-18 of FIG. 17;

FIG. 19 is a perspective view of yet another alternate embodiment of the closure device of the present invention;

FIG. 20 is an exploded view of the spherical retainers and sutures of FIG. 19;

FIG. 21 is a cross-sectional view taken along lines 21-21 of FIG. 19;

FIG. 22 is a cross-sectional view of a region of a covering member of an alternate embodiment of the present invention;

FIG. 23 is a close up view of the area of detail designated in FIG. 22;

FIG. 24 is a perspective view of another alternate embodiment of the closure device shown with the covering member plug separated from the covering member;

FIG. 25 is a perspective view of the assembled closure member of FIG. 24;

FIG. 26 is a top view of a region of the covering member of an alternative embodiment;

FIG. 27 is a bottom view of a region of the covering member of another alternative embodiment;

FIG. 29 is a side view of the closure device of FIG. 28;

FIG. 30 is a bottom view of the closure device of FIG. 28;

FIG. 31 is a cross-sectional view of the covering member of the closure device of FIG. 28;

FIG. 32 is a cross-sectional view illustrating attachment of the retainer and suture;

FIG. 33 is a cross-sectional view illustrating an alternate attachment of the retainer and suture;

FIG. 34 is a cross-sectional view illustrating another alternate attachment of the retainer and suture.

DETAILED DESCRIPTION OF PREFERRED EMBODIMENTS

Figure 28:
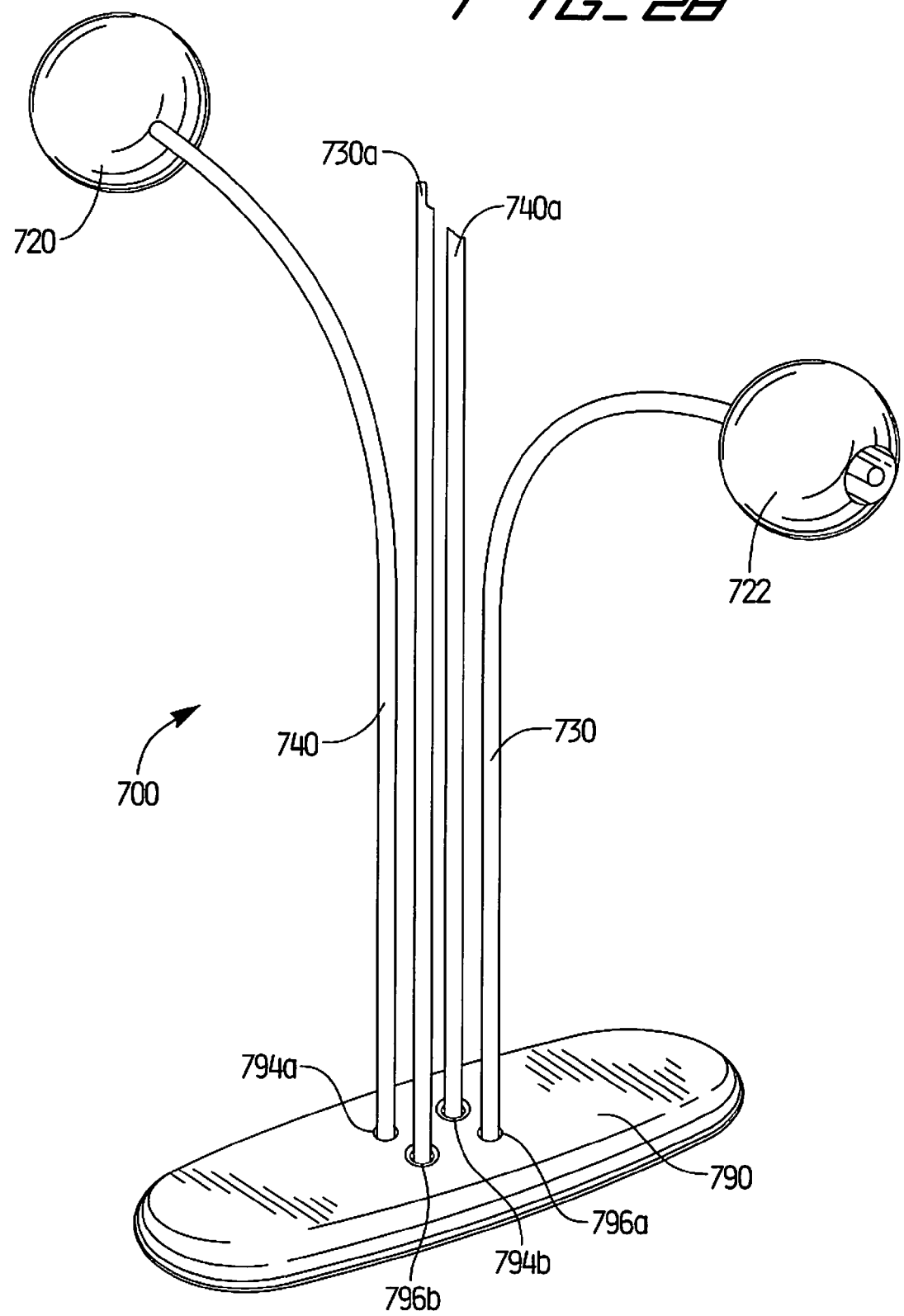
FIG. 28 is a perspective view of an alternate embodiment of the closure device of the present invention.

Referring now in detail to the drawings where like reference numerals identify similar or like components throughout the several views, FIG. 1 is a perspective view of a first embodiment of the vascular hole (aperture) closure device of the present invention. The device is intended to close an aperture in the vessel wall, typically formed after removal of a catheter previously inserted through the vessel wall into the vessel lumen for performing angioplasty or other interventional procedures. The aperture extends through the patient's skin and underlying tissue, through the external wall of the vessel, through the wall of the vessel, and through the internal wall of the vessel to communicate with the internal lumen of the vessel. The closure device of the present invention has an intravascular component to block blood flow and an extravascular component to retain the intravascular component.

More specifically, the closure device includes a covering member or patch positioned within the vessel against the internal wall of the vessel to block blood flow and two retainers positioned external of the vessel wall to retain the covering member in its blocking position. Each retainer is preferably spherical in configuration and is fixedly attached to a suture such that pulling of the suture advances the attached retainer toward the covering member to ultimately position the retainers in a side by side relationship either against or adjacent the external surface of the vessel wall.

Turning to FIGS. 1-7, a first embodiment of the closure device of the present invention is illustrated. Hole (aperture) closure device 10 has a covering (blocking) member or patch 40 and first and second retainers 20, 22. First and second retainers 20, 22 are preferably in the form of a sphere or ball. The covering member 40 is dimensioned and configured for positioning inside the vessel on the internal side of the vessel aperture against the internal wall of the vessel; the retainers 20, 22 are configured to be positioned outside the vessel wall adjacent or contiguous the external side of the vessel aperture.

Covering member 40, preferably elongated in configuration as shown, is retained in a delivery sheath in a longitudinal position for delivery to the vessel, and then pivots to a transverse position within the vessel lumen (substantially perpendicular to an axis extending through the aperture) for orientation to cover (patch) the vessel aperture on the internal side. This movement is illustrated in FIGS. 37A-37D of U.S. Pat. No. 7,662,161, the entire contents of which are incorporated herein by reference (hereinafter the '161 patent). A comparison of FIGS. 2 and 5 also shows pivoting of the covering member.

The spherical retainers are preferably held in the delivery tube in a stacked relationship (see e.g. FIG. 11), with retainer 22 (222) atop retainer 20 (220) (or vice versa).

The elongated covering member 40 functions to cover (patch) the internal opening in the vessel wall to prevent the egress of blood. With reference to FIGS. 1 and 4, the covering member 40 is preferably somewhat oval shaped with elongated substantially parallel side walls 42a, 42b and end walls 44a, 44b connecting the side walls 42a, 42b. Other shapes of the covering member are also contemplated. The end walls 44a, 44b can have substantially straight wall portions, or curved wall portions. Covering member preferably has a thicker region 43 in the central region than the first and second end regions 45, 47. Other dimensions are also contemplated.

The longitudinal axis of covering member 40 defines a lengthwise dimension and transverse axes define a shorter widthwise dimensions. The widthwise dimension of the covering member 40 is preferably, for a 6 Fr device, in the range of about 2.5 mm to about 3.5 mm, and more preferably about 3.3 mm. Other dimensions are also contemplated. The width preferably is at least substantially equal to the dimension of the internal opening in the vessel wall to effectively cover the opening. In a preferred embodiment, the covering member 40 has a length in the range of about 7.5 mm to about 9 mm (in a 6 French system), and preferably about 8 mm.

It should be appreciated that alternatively the covering member could be provided with an enlarged width region as illustrated in the embodiment of FIG. 1 of the '161 patent. The covering member could also be configured asymmetrically so that the enlarged region is off-centered to accommodate widening of the aperture as the member is pulled at an angle. The covering member could also be configured in a paddle shaped with a narrowed region adjacent a wider region as in FIGS. 9B-9E of the '161 patent. Other covering member configurations including those disclosed in the '161 patent could be utilized with the retainers of this present application.

The elongated covering member can be composed of materials such as polycarbonate or polyurethane. Preferably it is composed of resorbable materials such as lactide/glycolide copolymers that after a period of time resorb in the body. If composed of resorbable material, the covering member could optionally have regions of varying resorbability. Varying degrees of resorbability can be achieved for example by utilizing different materials having differing resorbable characteristics or by varying the mass of the covering member (increased mass increases resorbtion time).

Spherical retainers 20 and 22 are preferably composed of resorbable material. In a preferred embodiment, the diameter of each retainer 20, 22 is about 0.090 inches to about 0.095 inches, although other dimensions are contemplated. Although shown as spheres, other rounded shapes are also contemplated. The retainers could alternatively be made of non-absorbable polymeric or metallic material.

When the retainers 20 and 22 are released from the delivery instrument, they are spaced further from the covering member 40. They are then configured to be advanced toward the covering member 40. More specifically, each retainer 20, 22 is fixedly secured to a respective flexible connecting member such as suture 30, 32. Sutures 30, 32 are preferably made of polymeric material and are preferably resorbable, composed of a material such as polydioxanome. It is also contemplated that alternatively a metallic material could be utilized. The sutures, retainers and covering member can be made of the same or different resorbable material, and/or have the same or different resorption times.

As shown, suture 30 has a free end 30a and an opposite end 30b secured to retainer 20 by molding, gluing, forming a knot, or other methods. Similarly, suture 32 has a free end 32a and an opposite end 32b secured to retainer 22 in any of the foregoing manners. The suture is shown in the embodiment of FIG. 1 looped through the covering member. Other methods of attachment are also contemplated. For example, in the alternative embodiment of FIG. 8, sutures 150, 152 are attached to covering member 140 by a loop of suture 160. Loop 160 extends upwardly (proximally) from the covering member 140 and the sutures 150, 152 are looped through suture loop 160. Suture 160 can be attached to the covering member 140 by various methods such as insert molding or by tying a knot in the suture under the covering member. In another alternate embodiment shown in FIG. 24, sutures 180, 182 are insert molded to a plug 190. The covering member 192 has a recess 194 to receive the plug 190. During manufacture, the plug 190 is wedged within the recess 194, creating a tight frictional fit. The plug 190 is preferably flush with the distal surface 195 of covering member 192. Spherical retainers are designated by reference numerals 187, 188, are preferably identical to retainers 20, 22, and illustrated in the advanced position closer to proximal surface 197 of covering member 192.

To advance the retainers 20, 22 toward the vessel wall (and covering member), the free end of each suture is pulled proximally (in a direction of the arrow of FIG. 4, thereby moving the respective retainer in the opposite direction closer to the aperture A and vessel wall W. Once tightened against the tissue, a sufficient retention force is maintained, i.e. a proximal pulling force on the covering member 40 to pull it slightly proximally against the vessel wall. The retainers 20, 22 therefore help to prevent the covering member 40 from separating from the vessel wall (e.g. moving in the direction toward the opposing vessel wall) which could create an unwanted gap between the covering member 40 and the vessel opening to allow blood flow. The extent to which the retainers 20, 22 move toward the wall (and thus their distance from the vessel wall in their final placement position) will depend on the tissue thickness. Thus, the closure device can adjust for different tissue thicknesses and apply a constant retention force regardless of tissue thickness. The retainers of the other embodiments disclosed herein function in a similar manner.

The delivery instrument for inserting the closure device extends through an opening in the skin, through the tissue tract to the vessel, through an external opening in the vessel wall, through the aperture in the vessel wall, and through an internal opening on the internal side of the vessel wall into the vessel lumen.

The covering member 40 in FIG. 2 is outside retainer tube 50 and, within delivery sheath 60 in a tilted (pivoted) position. The covering member 40 emerges from the sheath 60 and moves from a tilted position, more aligned or in preferred embodiments substantially aligned with the longitudinal axis of the sheath, to a transverse position within the vessel (see FIG. 3). (Note the vessel wall is shown in FIG. 3 but the rest of the vessel and tissue are removed for clarity.) The retainers 20, 22 remain within tube 50. Note the covering member 40 can be ejected by a pusher (not shown) contacting the side or top wall. The retainers/covering members of the other embodiments disclosed herein can be delivered in a similar manner as that of retainers 20, 22 and covering member 40.

As shown in FIG. 4 covering member 40 is pulled proximally to abut the internal opening on the internal side of the vessel W to cover (patch) the opening and the sutures extend through the opening A in the vessel wall. The first retainer 20 is shown ejected from the delivery sheath 60 in FIG. 4 either by advancing the retainer, retracting the sheath after a counterforce is applied by engagement of the covering member with the vessel wall, or relative movement of both. The second retainer 22 is still within tube 50. The second retainer 22 is then deployed in a similar manner as retainer 20 and is shown outside sheath 60 in FIG. 5. Note that in the delivery position, the retainers 20 and 22 are preferably in a stacked relationship (such as in FIG. 11) to minimize the transverse dimension of the delivery system.

Then, to retain the covering member 40 in position against the vessel wall to block blood flow therethrough, sutures 30 and 32 are pulled proximally from their free ends 30a, 32a in the direction of arrows B of FIG. 6, thereby advancing the retainers 20, 22 distally in the direction of arrows C toward the vessel wall V and covering member 40. As shown, the retainers 20, 22 can be moved to a position contiguous to the vessel wall, or depending on tissue thickness, may be adjacent the wall with some tissue interposed between the retainers and vessel wall. The retainers 20, 22 in this position apply a proximal force on the elongated covering member 40 to limit movement of the covering member into the vessel. The retainers in this placement position are preferably in a substantially side by side relationship as shown in FIG. 7.

As shown in FIG. 7, in the side by side relationship, the retainers 20 and 22 are alongside in a transverse orientation with respect to covering member 40. That is, they are positioned along the width of the covering member 40. However it is also contemplated that the retainers in the placement position can be in a lengthwise orientation (substantially parallel to the longitudinal axis of the covering member) as shown in FIG. 9 where corresponding components to FIG. 7 (e.g. retainers 20', 22', sutures 30', 32', covering member 40') have prime designations. The retainers could also be in other side by side arrangements at angles to the longitudinal axis. Alternatively, the retainers can be partially stacked in the placement position.

FIG. 10 illustrates an alternate embodiment of the closure device, designated by reference numeral 200. Closure device is substantially identical to closure device of FIG. 1 except for the knot at the end of the suture to retain the suture. More specifically, suture 232 has a free end 232a and a knotted end 232b with a knot 236 to retain spherical retainer 222. Similarly, suture 240 has a free end 240a and a knotted end 240b with a knot 246 to retain spherical retainer 220. The sutures are held in frictional engagement with a bore extending through the respective retainer 220,222. Covering member 290 is substantially identical to covering member 40 of FIG. 1 with the sutures attached thereto by a loop (not shown) as in FIG. 1. As the suture free ends 240a, 232a are pulled, the respective spherical retainers 220, 222 are advanced toward the covering member 240, as the knots 246, 236 abut the proximal end of the respective spherical retainers 220 and 222. Thus, the knots aid in the attachment of retainers 220, 222.

FIGS. 11-13C illustrate schematically a delivery system which can be utilized for placement of the closure devices described herein and shows schematically the device of FIG. 10 by way of example.

The delivery device includes a retainer tube 350 which is positioned within a delivery sheath (not shown). Retainer tube 350 has a distal opening 352 communicating with lumen 354 providing for passage of the retainers 220, 222 of closure device 200. Also positioned within the delivery tube 350 is a pusher tube 360 which is preferably solid except for two small lumens (not shown) dimensioned to receive a respective suture 240, 232.

In use, the retainer tube 350 with the retainers of the closure device contained within is placed in a delivery sheath (not shown). When positioned within the delivery sheath, the retainers 220, 222 are contained within the lumen 352 and the covering member 290 is positioned outside the retainer tube 350, and held in a longitudinal position by the walls of the delivery sheath. The covering member 290 is advanced from the delivery sheath into the vessel lumen by advancing the pusher tube 360 against the second retainer 222 in the direction of the arrow of FIG. 11. Since in the delivery position the second retainer 222 abuts the first retainer 220 which abuts the covering member 290, advancement of the pusher tube 360 advances the covering member 290 from the delivery sheath.

Subsequently, the pusher tube 360 is moved further distally to advance the retainers 220, 222 from the retainer tube 350 as shown in FIG. 12. Next, the first retainer 220 is advanced toward the covering member as shown in FIGS. 13A, 13B by pulling the suture 240 from its proximal end in the direction of the arrow. After placement of the first retainer 220, the second suture 232 is pulled proximally in the direction of the arrow of FIG. 13C to advance the second retainer 222 toward the covering member 290. The sutures can then be severed leaving the retainers 220, 222 and covering member 290 in place. It should be appreciated that these schematic views of FIGS. 11-13C omit the surrounding tissue and vessel portions for clarity. The covering member 290 is positioned inside the vessel lumen and the spherical retainers 220, 222 are positioned outside the vessel lumen.

FIGS. 14-18 illustrate an alternate embodiment of the closure device having a configuration to restrict movement of the connecting member, e.g. the suture, which connects the retainer to the covering member.

More specifically, the closure device 400 of FIG. 14 is similar to the device 200 of FIG. 10 except the covering member 490 has a first pair of holes 494a, 494b and a second pair of holes 496a, 496b. The first pair of holes 494a, 494b receive suture 440 and the second pair of holes 496a, 496b receive suture 430. Holes 494a, 496a have a smaller diameter than holes 494b, 496b. The larger hole 494b is dimensioned to receive suture 440 for free unrestricted movement of the suture 440 therethrough and therefore easier application of spherical retainer 420. Similarly, the larger hole 496b is dimensioned to receive suture 430 for free unrestricted movement of the suture 430 therethrough and therefore for easier application (movement) of spherical retainer 422. Smaller hole 496a is dimensioned to frictionally engage suture 430 so that tension is applied to the suture 430. It is dimensioned so that the suture 430 can be pulled through the hole 496a if sufficient force is applied by pulling on free end 430a, but if such predetermined force is not applied, the suture will remain frictionally engaged within the wall of the opening 496a and not move. In this manner, when the user ceases pulling on free end 430a, the suture 430 and thus the spherical retaining ball 422 will remain in position. Suture 440 operates in a similar manner, with smaller opening 494a dimensioned to frictionally engage and resist movement of the suture 440 to retain spherical retainer 420. FIGS. 15-18 show how the suture is looped through the respective opening.

In an alternate embodiment, a plurality of internal teeth can be provided to enhance the retention of the suture within the smaller diameter hole. This is shown for example in FIGS. 22 and 23 wherein hole 496a' has a plurality of teeth 497 formed on the interior wall of the smaller opening. Engagement of the suture 430' by the teeth 497 retains the suture 430 and spherical retainer. Note that the teeth 497 can be formed to angle inwardly so the suture 430 can be moved in only one direction, i.e. proximally so the retainer is advanced toward the covering member. Similar teeth can be provided in the other small hole for retaining the other suture and retainer.

In the embodiment of FIG. 26, the opening 522 in covering member 520 has a triangular wedge shape region 523. The region 523 has a reduced size opening, narrowing to a diameter less than an outer diameter of the suture 530 extending therethrough. The clinician can move the suture 530 into the narrow (reduced diameter) region 523 when desired to apply a gripping force on the suture 530 to retain the suture in place. Opening 524 is dimensioned larger than the outer diameter of the suture 530 to allow free unrestricted movement therethrough. Only one of the pair of openings is shown in the portion of the covering member 520 illustrated in FIG. 26, it being understood that a second similar pair of openings for the second suture can be provided. In all other respects the closure device can be identical to closure device 200 of FIG. 10 or other devices disclosed herein.

In the embodiment of FIG. 27, the retention of the suture is enhanced by inwardly directed bumps 560a, 560b, 560c and 560d on the underside of the covering member 570. That is, the suture (not shown) extending through large and small openings 570, 572, respectively, is gripped by the bumps 560a, 560b as the distance between opposing bumps is slightly less than the diameter of the suture. Sufficient tension (e.g. pulling force by the clinician), overrides the frictional force of the bumps 560 on the suture. Similarly a suture (not shown) extending through large and small openings 574, 576 is frictionally restrained by bumps 560c, 560d. The sutures connect retainers to the covering member 550 and are configured to be pulled to advance the retainers to the covering member in the manner described above with respect to the other embodiments. The bumps 560 can be utilized as a supplement to the small opening frictional engagement as is the embodiment of FIG. 14 or alternatively as the sole retention feature with two pairs of larger openings in the covering member.

FIGS. 19-21 illustrate an alternate embodiment of the closure device, designated generally by reference numeral 600, having a suture 610 extending transversely and joining spherical retainers 620 and 622. A knot 610a, 610b is formed on each end of the suture 610 to retain the retainers 620, 622. Connecting suture 630 has a looped proximal end 632 through which suture 610 extends. This loop 632 is tightened to secure suture 610. Both ends 631, 632 of the looped suture 630 extend though first opening 641 in covering member 640. End 632 terminates in knot 633 to connect suture 630 to covering member 640 (due to its diameter larger than opening 641). The other end 637 loops through covering member 640, exiting through opening 642 in suture portion 635.

Openings 642, 641 can be large and small openings functioning similar to the large and small openings of the embodiment of FIG. 14. That is, the openings can be configured to provide for free movement and tighter frictional engagement as in the embodiment of FIG. 14.

Pulling of suture end 630a advances the retainers 620, 622 together toward the covering member 640 due to the engagement of suture 630 with the transverse suture 610.

FIGS. 28-31 illustrate an alternate embodiment of the closure device, designated generally by reference numeral 700. Device 700 is similar to device 400 except for the way the suture and retainer are attached and the suture openings in the covering member. More specifically, closure device 700 has a first suture 730 and a second suture 740. Retainer 722, preferably spherical in configuration, is connected to suture 730 and retainer 720, preferably spherical, is connected to suture 740.

Covering member 790 has a first pair of holes 794a, 794b and a second pair of holes 796a, 796b. The first pair of holes 794a, 794b receive suture 740 and the second pair of holes 796a, 796b receive suture 730. Holes 794a, 796a have a smaller diameter than holes 794b, 796b. The larger hole 794b is dimensioned to receive suture 740 for free unrestricted movement of the suture 740 therethrough and therefore easier application of spherical retainer 720. Similarly, the larger hole 796b is dimensioned to receive suture 730 for free unrestricted movement of the suture 730 therethrough and therefore for easier application (movement) of spherical retainer 722.

Smaller hole 796a is dimensioned to frictionally engage suture 730 so that tension is applied to the suture 730. It is dimensioned so that the suture 730 can be pulled through the hole 796a if sufficient force is applied by pulling on free end 730a, but if such predetermined force is not applied, the suture will remain frictionally engaged within the wall of the opening 796a and not move. As shown in the cross-sectional view of FIG. 31, the hole 796a has an inwardly angled wall 797 transitioning into a reduced diameter region 798 and an outwardly angled wall 799 transitioning back to a larger diameter. The angled walls 797, 799 facilitate movement of the suture 730 when tension is applied, with the reduced diameter region 798 frictionally securing the suture. Hole 794a has a similar configuration as hole 796a and thus contains similar angled walls. In this manner, when the user ceases pulling on free end 730a, the suture 730 and thus the spherical retaining ball 722 will remain in position. Suture 740 operates in a similar manner, with smaller opening 794a dimensioned to frictionally engage and resist movement of the suture 740 to retain spherical retainer 720.

FIG. 32 illustrates one method of attachment of the suture to a spherical retainer. Spherical retainer 720 has a through hole 721 extending therethrough. Hole 721 has a first portion 721a having a first diameter and a second portion 721b having a second larger diameter. A crimp or a bead 743 is attached to the suture 740, creating a diameter larger than the diameter of portion 721a. Thus, the wall of the through hole 721 forms a shoulder 723 to block movement of the spherical retainer 720. Preferably, the end 741 of the suture is substantially flush with the spherical retainer 720. The crimp or bead is of substantial transverse dimension to frictionally engage the second portion 721b. Consequently, this frictional engagement prevents the retainer 720 from sliding in the direction away from the covering member 790 while the shoulder 723 prevents the retainer 720 from sliding in the direction toward the covering member 790. The retainer 722 and suture 730 preferably have the same structure and engagement/retention as retainer 722 and suture 740.

In the alternate embodiment of FIG. 33, the suture 740' has a knot 747 formed at its end. The shoulder 723' provides a stop for movement of retainer 720' away from covering member 790', as the diameter of portion 721a' of opening 721 is less than the transverse dimension of the knot 747. The knot 747 is of sufficient transverse dimension to frictionally engage the second portion 721b' to prevent the retainer 720' from sliding in the direction away from the covering member 790.

Figure 35:
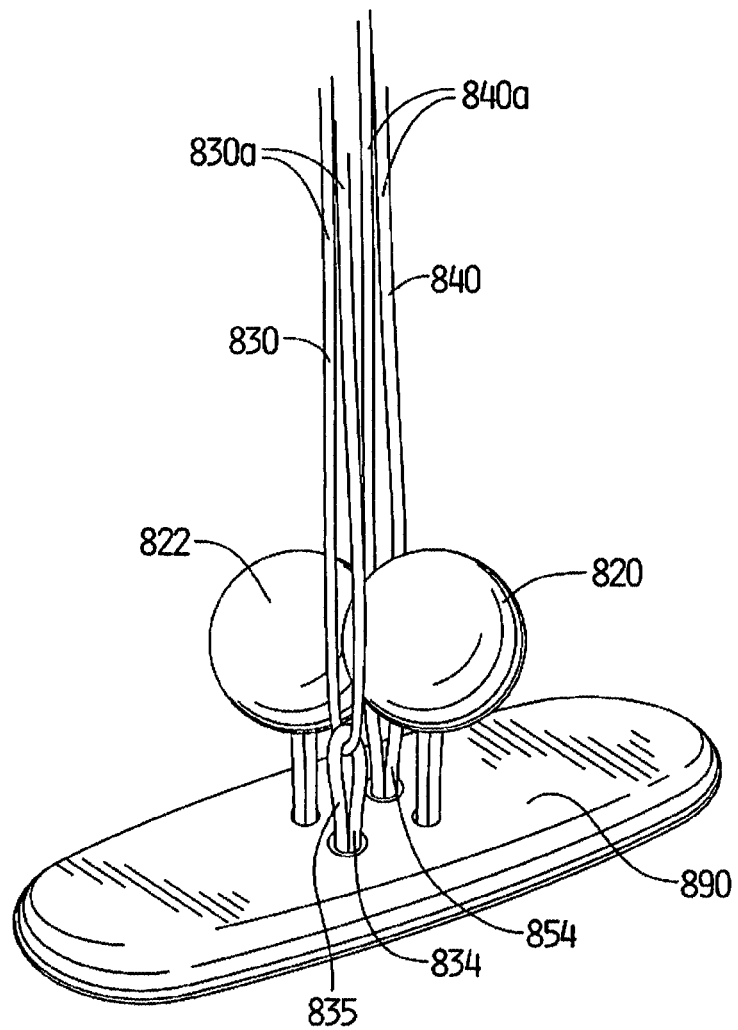
FIG. 35 is a perspective view of another alternate embodiment of the closure device of the present invention utilizing the retainer/suture attachment of FIG. 34.

In the embodiment of FIGS. 34 and 35, a suture 834 forming a loop 835 has a knot 837 at one end. This suture knot 837 frictionally engages portion 821b of the hole 821 formed in the retainer 820. A reduced diameter hole portion 821a forms a shoulder 823 to block movement of the knot 837. As shown, the looped end 835 of suture 834 receives suture 830. Consequently, tension applied to the ends 830a of suture 830 pull the loop 835 upwardly (as viewed in the orientation of the FIG. 35) away from the covering member 890 to advance spherical retainer member 822 toward the covering member 890. A second suture 854 identical to suture 834 has a loop to receive suture 840 in the same manner as suture 830. Suture 854 and 840 are identical to sutures 834 and 830, respectively, except that they function to secure and move spherical retainer member 820. Consequently, when the ends 840a of suture 840 are pulled proximally, the suture 854, attached within an opening in the retainer 820 in the identical manner as suture 834, pulls the retainer 820 toward the covering member 890.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A device for closing an aperture in a vessel wall, the aperture having an external opening in an external region of the vessel wall and an internal opening in an internal region of the vessel wall, the device comprising:
   a distal covering member positionable inside the vessel against the internal opening of the aperture, the covering member having a dimension to prevent egress of fluid through the aperture, the covering member having a first opening and a second opening spaced from the first opening;
   a proximal first retainer positionable external of the vessel and engageable with tissue to retain the distal covering member;
   a second retainer movable toward the covering member, the second retainer being movable independently of the first retainer;
   a flexible connecting member operatively connecting the covering member and the first retainer for placement of the closure device to close the aperture in the vessel wall, the first retainer fixedly secured to the flexible connecting member, the flexible connecting member advancing the first retainer toward the covering member, the first opening of the covering member configured to frictionally engage the flexible connecting member to restrict movement of the flexible connecting member until a predetermined force is applied which enables the flexible connecting member to move through the first opening, and the second opening having a larger diameter than the first opening for unrestricted movement of the flexible connecting member, wherein movement of the flexible connecting member in a proximal direction away from the covering member advances the first retainer toward the covering member in a distal direction as the flexible connecting member is moved through the first opening; and
   a second flexible connecting member, the second retainer attached to the second flexible connecting member and pulling of the second flexible connecting member advances the second retainer toward the covering member, the covering member having a third opening configured to restrict movement of the second flexible connecting member, and the second flexible connecting member is advanceable through the third opening until a predetermined force is applied and is not advanceable through the third opening if the predetermined force is not applied.

2. The device of claim 1, wherein the flexible connecting member comprises a first suture.

3. The device of claim 2, wherein the first retainer is spherical in configuration.

4. The device of claim 1, wherein the second retainer is spherical in configuration.

5. The device of claim 1, wherein the covering member is composed of a polymeric material.

6. The device of claim 1, wherein the covering member and first retainer are composed of a resorbable material.

7. The device of claim 1, wherein the covering member is pivotable between a more longitudinal orientation for delivery and a transverse position for placement.

8. The device of claim 1, wherein the flexible connecting member has a first portion, a second free end portion, and an intermediate portion positioned between the first portion and the second portion, the first retainer is secured to the first portion and the intermediate portion loops through the covering member.

9. A device for closing an aperture in a vessel wall, the aperture having an external opening in an external region of the vessel wall and an internal opening in an internal region of the vessel wall, the device comprising:
a distal covering member positionable inside the vessel against the internal opening of the aperture, the covering member having a dimension to prevent egress of fluid through the aperture, the covering member having a first opening and a second opening spaced from the first opening;
a proximal first retainer positionable external of the vessel and engageable with tissue to retain the distal covering member;
a flexible connecting member operatively connecting the covering member and the first retainer for placement of the closure device to close the aperture in the vessel wall, the first retainer fixedly secured to the flexible connecting member, the flexible connecting member advancing the first retainer toward the covering member, the first opening of the covering member configured to frictionally engage the flexible connecting member to restrict movement of the flexible connecting member until a predetermined force is applied which enables the flexible connecting member to move through the first opening, and the second opening having a larger diameter than the first opening for unrestricted movement of the flexible connecting member, wherein movement of the flexible connecting member in a proximal direction away from the covering member advances the first retainer toward the covering member in a distal direction as the flexible connecting member is moved through the first opening, the flexible connecting member composed of a first suture;
a second suture and a second retainer attached to the second suture, the second suture advancing the second retainer toward the covering member; and
the first and second retainers are positioned in a substantially side by side non-stacked relationship in a placement position and are positioned in a stacked relationship one above the other in a delivery position.

10. The device of claim 9, wherein the covering member has a third opening configured to restrict movement of the second suture, and the second suture is advanceable through the third opening until a predetermined force is applied and is not advanceable through the third opening if the predetermined force is not applied.

11. The device of claim 10, further comprising a fourth opening in the covering member for unrestricted movement of the second suture.

12. The device of claim 9, wherein the first and second retainers and the first and second sutures are composed of a resorbable material.

13. The device of claim 9, wherein the covering member has a third opening having a first diameter smaller than a second diameter of a fourth opening to frictionally engage the second suture to restrict movement of the second suture.

14. A device for closing an aperture in a vessel wall, the aperture having an external opening in an external region of the vessel wall and an internal opening in an internal region of the vessel wall, the device comprising:
a distal covering member positionable inside the vessel against the internal opening of the aperture, the covering member having a dimension to prevent egress of fluid through the aperture, the covering member having a first opening and a second opening spaced from the first opening;
a proximal first retainer positionable external of the vessel and engageable with tissue to retain the distal covering member;
a flexible connecting member operatively connecting the covering member and the first retainer for placement of the closure device to close the aperture in the vessel wall, the first retainer fixedly secured to the flexible connecting member, the flexible connecting member advancing the first retainer toward the covering member, the first opening of the covering member configured to frictionally engage the flexible connecting member to restrict movement of the flexible connecting member until a predetermined force is applied which enables the flexible connecting member to move through the first opening, and the second opening having a larger diameter than the first opening for unrestricted movement of the flexible connecting member, wherein movement of the flexible connecting member in a proximal direction away from the covering member advances the first retainer toward the covering member in a distal direction as the flexible connecting member is moved through the first opening, the flexible connecting member composed of a first suture;
a second suture and a second retainer attached to the second suture, the second suture advancing the second retainer toward the covering member; and
wherein in a placement position the first and second retainers are in a substantially side by side non-stacked relationship and in a transverse orientation with respect to the covering member.

* * * * *